United States Patent [19]

Kovacevic et al.

[11] Patent Number: 4,559,300

[45] Date of Patent: Dec. 17, 1985

[54] METHOD FOR USING AN HOMOLOGOUS BACILLUS PROMOTER AND ASSOCIATED NATURAL OR MODIFIED RIBOSOME BINDING SITE-CONTAINING DNA SEQUENCE IN STREPTOMYCES

[75] Inventors: Steven Kovacevic; Jeffrey T. Fayerman; James R. Miller; Mark A. Richardson, all of Indianapolis, Ind.

[73] Assignee: Eli Lilly and Company, Indianapolis, Ind.

[21] Appl. No.: 458,803

[22] Filed: Jan. 18, 1983

[51] Int. Cl.$^4$ .................. C12P 21/00; C12N 15/00; C12N 1/20; C12N 1/00

[52] U.S. Cl. .................. 435/68; 435/172.3; 435/253; 435/317; 935/11; 935/29; 935/75; 536/27

[58] Field of Search .............. 435/68, 70, 91, 253, 435/172.3, 172, 317; 935/11, 29, 75

[56] References Cited

U.S. PATENT DOCUMENTS

| | | | |
|---|---|---|---|
| 344,710 | 6/1886 | Bennett | 24/93 |
| 4,273,875 | 6/1981 | Manis | 435/317 X |
| 4,360,597 | 11/1982 | Bibb et al. | 435/317 X |
| 4,416,994 | 11/1983 | Nakatsukasa et al. | 435/317 X |
| 4,436,815 | 3/1984 | Hershberger et al. | 435/172.3 |
| 4,460,688 | 7/1984 | Sanders et al. | 935/75 |

FOREIGN PATENT DOCUMENTS

| | | |
|---|---|---|
| 0036259 | 9/1981 | European Pat. Off. . |
| 0038156 | 10/1981 | European Pat. Off. .............. 435/91 |
| 0063953 | 11/1981 | European Pat. Off. .............. 435/172 |
| 0052002 | 5/1982 | European Pat. Off. .............. 435/70 |
| 057976 | 12/1982 | European Pat. Off. . |
| 2044773 | 10/1980 | United Kingdom .............. 435/172 |

OTHER PUBLICATIONS

Moran, Jr., et al., *Molecular and General Genetics*, 1982, vol. 186, pp. 339–346.
Palva, I., 1982, Gene 19:81.
Palva, I. et al., 1982, Proc. Nat'l. Acad. Sci., USA, 79:5582.
Derwent Abstract, 37323, E/19-Abstract of Belgium No. BE-891-659.
Bibb and Cohen, 1982, Mol. Gen. Genet., 187:265–277.
Westpheling, et al., 1985, Nature, vol. 313.

*Primary Examiner*—Alvin E. Tanenholtz
*Assistant Examiner*—Jayme A. Huleatt
*Attorney, Agent, or Firm*—Gerald V. Dahling; Arthur R. Whale

[57] ABSTRACT

A method for expressing a functional polypeptide in Streptomyces comprises transforming a Streptomyces host cell with a recombinant DNA expression vector and then culturing the transformed cell under conditions suitable for cell growth. The recombinant DNA expression vector comprises the veg or any other homologous Bacillus promoter, a naturally occurring or modified ribosome binding site-containing DNA sequence and a gene that codes for a functional polypeptide such as human pre-proinsulin. The method is specifically exemplified by use of expression plasmids pOW529, pOW539 and transformants, *Streptomyces ambofaciens*/pOW529 and *Streptomyces ambofaciens*/pOW539. The method is broadly applicable and is particularly useful in economically important Streptomyces taxa.

58 Claims, 6 Drawing Figures

Restriction Site Map of Plasmids
pOW 527 and pOW 528**

1. pOW 527 (~12.8 kb)
2. pOW 528 (~12.8 kb)

Restriction Site Map of Plasmids pOW 529 and pOW 530

1. pOW 529 ~ 18.6 kb
2. pOW 530 ~ 18.6 kb

Restriction Site Map of Plasmids pOW 539 and pOW 540

1. pOW 539 (~17 kb)
2. pOW 540 (~17 kb)

Synthesis Procedure for Fragment T₁

Restriction Site Map of Plasmids pEL 107 and pEL 105 pEL107 pEL105

Restriction Site Map of Plasmids
pBS 1 and pBS 3** pBS 1 pBS 3

METHOD FOR USING AN HOMOLOGOUS BACILLUS PROMOTER AND ASSOCIATED NATURAL OR MODIFIED RIBOSOME BINDING SITE-CONTAINING DNA SEQUENCE IN STREPTOMYCES

The present invention comprises a method for using an homologous Bacillus promoter and associated natural or modified ribosome binding site-containing DNA sequence for expression of a functional polypeptide in Streptomyces. The invention further comprises the transformants which are required to employ the aforementioned method.

The present invention provides a method for expressing functional polypeptides in Streptomyces host cells by means of recombinant DNA technology. Heretofore, the development and exploitation of recombinant DNA technology in Streptomyces have been retarded and made especially difficult because of the general lack of suitable cloning and expression vectors. This paucity of expression vectors is explained in part by the lack of recognition afforded foreign transcription and translation initiation signals in Steptomyces. Consequently, the well known trp (Hallewell, R. A. and S. Emtage, 1980, Gene 9:27), lac (Guarante, L. et al., 1980, Cell 20:543 and Roberts, T. M. et al., 1979, Proc. Nat. Acad. Sci USA 76:5596), lpp (Lee, N. et al., 1981, J. of Bacteriol. 146:861; Zwiebel, L. J. et al., 1981, J. of Bacteriol. 145:654 and Nakamura, K. and M. Inouye, 1979, Cell 18:1109) and Bacteriophage $\lambda P_L$ (Derom, C. et al., 1982, Gene 17:45; Remaut, E. et al., 1981, Gene 15(1):81 and Bernard, H. et al., 1979, Gene 5:59) transcription and translation-directing promoter systems are not functional in Streptomyces. Thus, few foreign and practically no eukaryotic genes have been expressed in the Streptomyces host system.

The extremely limited ability of Streptomyces to recognize foreign transcription and translation signals necessitates the development of alternate signals that are recognized. Accordingly, a *Bacillus subtilis* promoter- and translation signal-containing sequence, and certain modifications thereof, were engineered to be useful for directing the expression of virtually any polypeptide in Streptomyces. This method for expressing polypeptides in Streptomyces represents a significant advance in the technical art and greatly expands the application of recombinant DNA technology in gram positive microorganisms.

Gene cloning and expression of products in Streptomyces are highly advantageous since the organism is substantially non-pathogenic and ordinarily does not produce endotoxins. In addition, Streptomyces has been extensively studied and is well known and understood in the antibiotic and fermentation industries. The present method and associated expression vectors and transformants are particularly important because they allow for the commercial exploitation of these important advantages.

For purposes of the present invention, as disclosed and claimed herein, the following terms are as defined below.

Recombinant DNA Expression Vector—any autonomously replicating agent, including but not limited to plasmids, comprising a DNA molecule to which one or more additional DNA segments can or have been added.

Transformation—the introduction of DNA into a recipient host cell that changes the genotype and consequently results in a change in the recipient cell.

Transformant—a recipient host cell that has undergone transformation.

Restriction Fragment—any linear portion or whole of plasmid or chromosomal DNA generated by the action of one or more restriction enzymes.

Functional Polypeptide—a recoverable bio-active entirely heterologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bioinactivating homologous polypeptide which can be specifically cleaved.

Fused Gene Product—a recoverable heterologous polypeptide which is fused with a portion or whole of a homologous polypeptide.

Insertional Isomer—one of the two or more possible recombinant DNA molecules formed when a DNA fragment is inserted at one of two or more compatible sites on the recipient DNA.

DETAILED DESCRIPTION OF THE INVENTION

Figure 1:
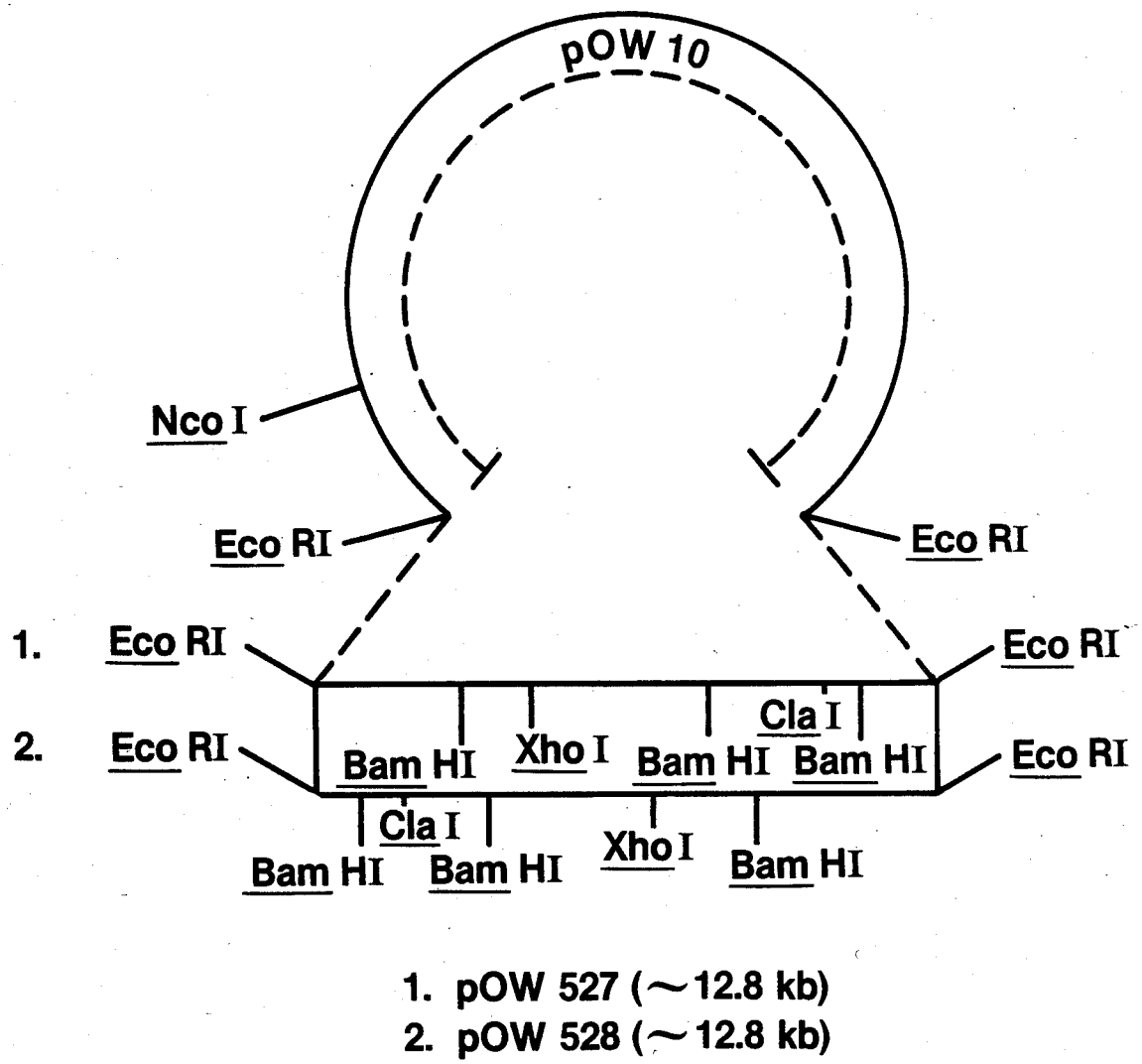

The present invention is a method for expressing a functional polypeptide in Streptomyces comprising transforming a Streptomyces host cell with a recombinant DNA expression vector, said vector comprising
(1) a homologous Bacillus promoter,
(2) a naturally occurring or modified Bacillus ribosome binding site-containing DNA sequence, and
(3) a gene encoding a functional polypeptide and culturing said transformed Streptomyces cell under growing conditions, subject to the limitations that said vector replicates and is selectable in said transformed Streptomyces cell and that said promoter and said DNA sequence direct transcription and expression of said gene in said transformed Streptomyces host cell. The invention further comprises the transformants which are required to employ the aforementioned method.

More particularly, the above method of the present invention is exemplified by transforming a Streptomyces host cell with a recombinant DNA expression vector which comprises
(1) the ribosome binding site-containing DNA sequence

wherein
A is deoxyadenyl,
G is deoxyguanyl,
C is deoxycytosyl,
T is thymidyl,
R is G or C,
$R^1$ is G or C, and
$R^2$ is G or T,
(2) the veg promoter of *Bacillus subtilis*, and
(3) a gene that encodes a functional polypeptide and culturing said transformed Streptomyces cell under growing conditions, subject to the further limitation that (1) R and $R^1$ are not simultaneously the same deoxyribonucleotide and (2) when $R^2$ is T, then R is G and $R^1$ is C.

The ribosome binding site-containing DNA sequence wherein R and $R^1$ are G or C, wherein $R^2$ is G and to which the veg promoter and gene are ligated, can be conventionally synthesized by the modified phosphotriester method, using fully protected trideoxyribonucleotide building blocks, in substantial accordance with the procedures of Itakura et al., 1977, Science 198:1056 and Crea et al., 1978, Proc. Nat. Acad. Sci. USA 75:5765. The veg promoter can either be synthesized directly or obtained by EcoRI-SfaNI digestion of plasmid pMS480. The resultant ~0.38 kb EcoRI-SfaNI fragment contains the veg promoter as well as additional deoxyribonucleotides at the 5' end of the coding strand (adjacent to the EcoRI sticky terminus). The veg promoter and ribosome binding site-containing DNA sequence wherein $R^2$ is T can be obtained by EcoRI-BamHI digestion of plasmid pMS480. The resultant ~0.48 kb EcoRI-BamHI fragment contains the aforementioned additional deoxyribonucleotides as well as deoxyribonucleotides at the 3' end of the coding strand which encode a portion of a homologous *Bacillus subtilis* polypeptide. Plasmid pMS480 is ~4.8 kb and can be conventionally isolated from *E. coli* K12 JA221/pMS480, a strain deposited and made part of the permanent stock culture collection of the Northern Regional Research Laboratory, Peoria, Ill. The strain is available to the public as a preferred source and stock reservoir of plasmid pMS480 under the accession number NRRL B-15258.

For convenience and ease of construction, the veg promotor was obtained by EcoRI-SfaNI digestion of plasmid pMS480. The resultant fragment was then ligated to the aforedescribed ribosome binding site-containing DNA sequence wherein R and $R^1$ are G or C and wherein $R^2$ is G. This sequence was designed to have SfaNI and NcoI sticky ends. The sequence thus allows for the direct expression of a polypeptide upon simultaneous ligation with both a NcoI-restricted gene and the aforementioned ~0.38 kb EcoRI-SfaNI veg promoter-containing fragment. Direct expression results because the ligation of the NcoI sticky ends restores the ATG translational start triplet of the NcoI-restricted gene. The synthetic sequence is therefore useful for the universal direct expression, under the control of the *Bacillus subtilis* veg promoter, in Streptomyces of any gene that encodes a functional polypeptide.

Although genes that naturally contain a NcoI site at the translational start point are preferred, genes lacking such sites can also be used. In the latter case, the gene can be cleaved by a restriction enzyme and then reconstructed synthetically (Itakura et al., 1977 and Crea et al., 1978) so as to contain the desired NcoI sticky end. Alternatively, depending upon convenience and ease of construction, the modified gene may be entirely synthetic. In either case, the modified gene can be ligated to the NcoI sticky end of the aforementioned ribosome binding site-containing sequence thus restoring the ATG methionine-encoding start triplet and thus allowing for the direct expression in Streptomyces of a desired product.

Ligation of a functional polypeptide-encoding gene at the BamHI restriction site of the ~0.48 kb EcoRI-BamHI fragment allows for expression of a fused gene product. Although genes that naturally contain a BamHI site at or near the translational start point are preferred, genes lacking such sites can also be used. In the latter case, the gene can be cleaved by a restriction enzyme and then reconstructed synthetically so as to contain the desired BamHI sticky end.

The present method for expressing a functional polypeptide in Streptomyces represents a significant technical advance. The aforedescribed Bacillus promoter and ribosome binding site-containing DNA sequence can be used for the universal expression in Streptomyces of any polypeptide-encoding gene.

Expression vectors useful for illustrating the present invention were constructed by ligating the ~0.38 kb EcoRI-SfaNI fragment of plasmid pMS480, the ~4 kb EcoRI-NcoI fragment of the pre-proinsulin plasmid pOW601 and the aforementioned ribosome binding site-containing DNA sequence. The resultant plasmid, designated as pOW10, is functional in *E. coli* and comprises a functional polypeptide-encoding gene in translational reading phase with the veg promoter. Plasmid pOW10 is particularly useful for constructing expression vectors that are functional in Streptomyces and therefore illustrative of the present method.

Plasmid pOW601, which is used as a starting material for constructing plasmid pOW10, is ~4.4 kb and can be conventionally isolated from *E. coli* K12 JA221/pOW601, a strain deposited and made part of the permanent stock culture collection of the Northern Regional Research Laboratory, Peoria, Ill. The strain is available to the public as a preferred source and stock reservoir of the plasmid under the accession number NRRL B-15259.

Illustrative vectors that are functional in Streptomyces are constructed by ligating EcoRI-digested plasmid pOW10 into EcoRI-digested plasmid pBS1. Ligation of EcoRI-digested plasmid pOW10 into EcoRI-digested plasmid pBS1 results in the illustrative ~12.8 kb plasmids pOW527 and pOW528. Plasmid pBS1 is constructed by ligating the ~3.9 kb BamHI fragment of plasmid pHI-18 into the ~4.4 kb BamHI fragment of plasmid pEL105. Plasmid pHI-18 is ~3.9 kb and contains a chloramphenicol resistance gene as well as an origin of replication that is functional in Bacillus. Plasmid pHI-18 is constructed by an ~0.7 kb HpaII deletion of plasmid pHI-16. The latter plasmid is an in vivo deletion of known chimeric plasmid pBD12 (disclosed in Gryczan et al., 1980, J. Bacteriology 141(1):246) which can be conventionally isolated from *Bacillus subtilis* MI112/pHI-16, a constructed strain deposited and made part of the permanent stock culture collection of the Northern Regional Research Laboratory, Peoria, Ill. The strain is available to the public as a preferred source and stock reservoir of the plasmid under the accession number NRRL B-12597. Plasmid pEL105 is constructed by ligating the ~1.6 kb BamHI fragment of plasmid pLR2 (constructed by ligating HindIII-digested plasmid pIJ6 (disclosed in Thompson et al., 1980, Nature 286:525), and HindIII-digested plasmid pBR322), into the ~2.8 kb BamHI fragment of plasmid pEL103. The latter plasmid can be conventionally isolated from *Streptomyces granuloruber* No. A39912.13/pEL103, a strain deposited and made part of the permanent stock culture collection of the Northern Regional Research Laboratory, Peoria, Ill. The strain is available as a preferred source and stock reservoir of the plasmid under the accession number NRRL 12549. A restriction site map of each of plasmids pOW527 and pOW528 is presented in FIG. 1 of the accompanying drawings.

Plasmids pOW527 and pOW528 are functional in Streptomyces, comprise a functional pre-proinsulin-encoding gene in translational reading phase with the veg promoter and ribosome binding site-containing synthetic DNA sequence wherein R is G, $R^1$ is C and $R^2$ is G, and therefore are useful for exemplifying the present invention. Other vectors useful for exemplifying the present method were constructed by (1) digesting plasmid pOW10 with NcoI and plasmid pMC1403 with BamHI restriction enzyme; (2) filling in the resulting sticky ends with the Klenow fragment of DNA polymerase; (3) disgesting the filled-in fragments with EcoRI restriction enzyme and (4) ligating the resultant two fragments at their respective EcoRI and blunted ends. Plasmid pMC1403, which is used as a starting material for these constructions, is ~9.9 kb and contains a portion of the lacZ gene. The plasmid can be conventionally isolated from *E. coli* K12 BE904/pMC1403, a strain deposited and made part of the permanent stock culture collection of the Northern Regional Research Laboratory, Peoria Ill. The strain is available to the public as a preferred source and stock reservoir of the plasmid under the accession number NRRL B-15213. The aforementioned ligation restores both the NcoI and BamHI restriction sites and therefore results in a plasmid, designated as plasmid pOW303, which contains a portion of the lacZ gene in translational reading phase with the veg promoter and ribosome binding site-containing synthetic DNA sequence.

Figure 2:
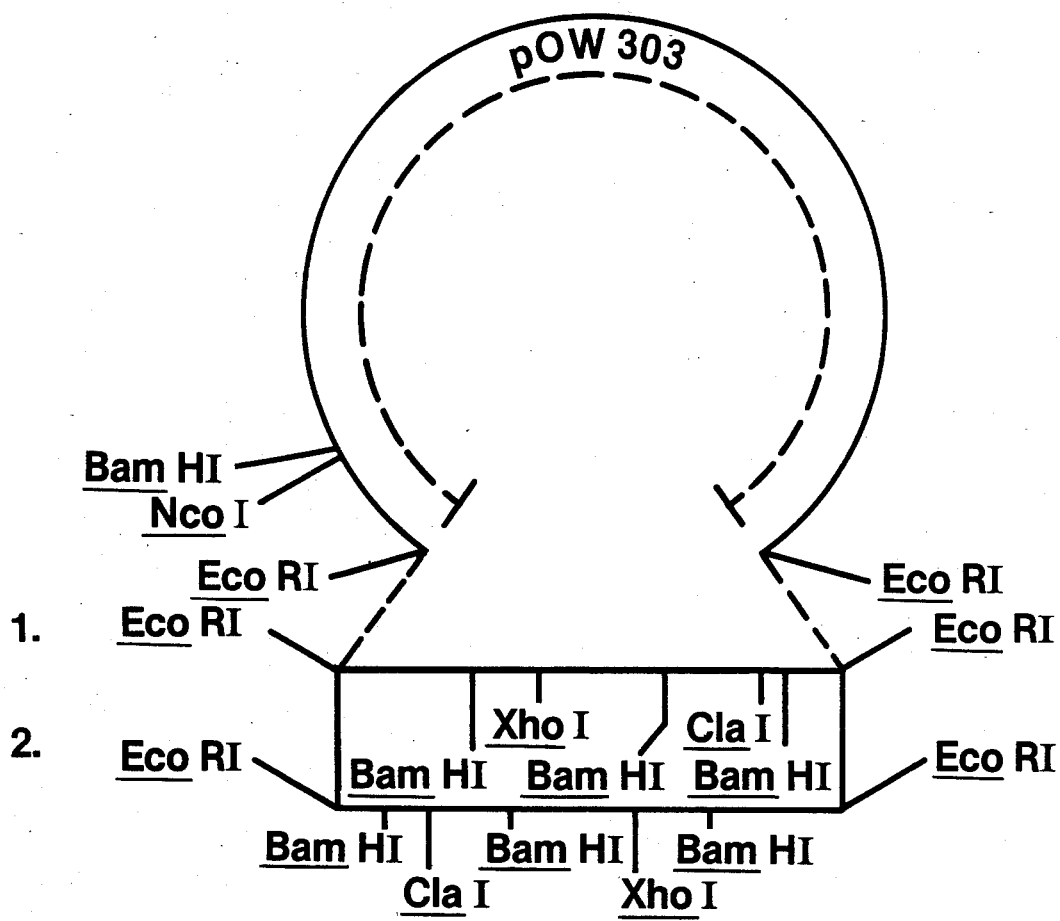

Plasmid pOW303 was digested with EcoRI restriction enzyme and ligated to EcoRI-digested plasmid pBS1 to produce the illustrative plasmids pOW529 and pOW530. Plasmids pOW529 and pOW530 are functional in Streptomyces, comprise a functional polypeptide-encoding gene in translational reading phase with the veg promoter and aforementioned DNA sequence wherein R is G, $R^1$ is C and $R^2$ is G, and therefore are useful for further illustrating the present invention. The β-galactosidase activity conferred to host cells by the aforementioned vectors can be employed as a selectable marker making the vectors generally useful for molecular cloning. Restriction site maps of each of plasmids pOW529 and pOW530 is presented in FIG. 2 of the accompanying drawings.

Figure 3:
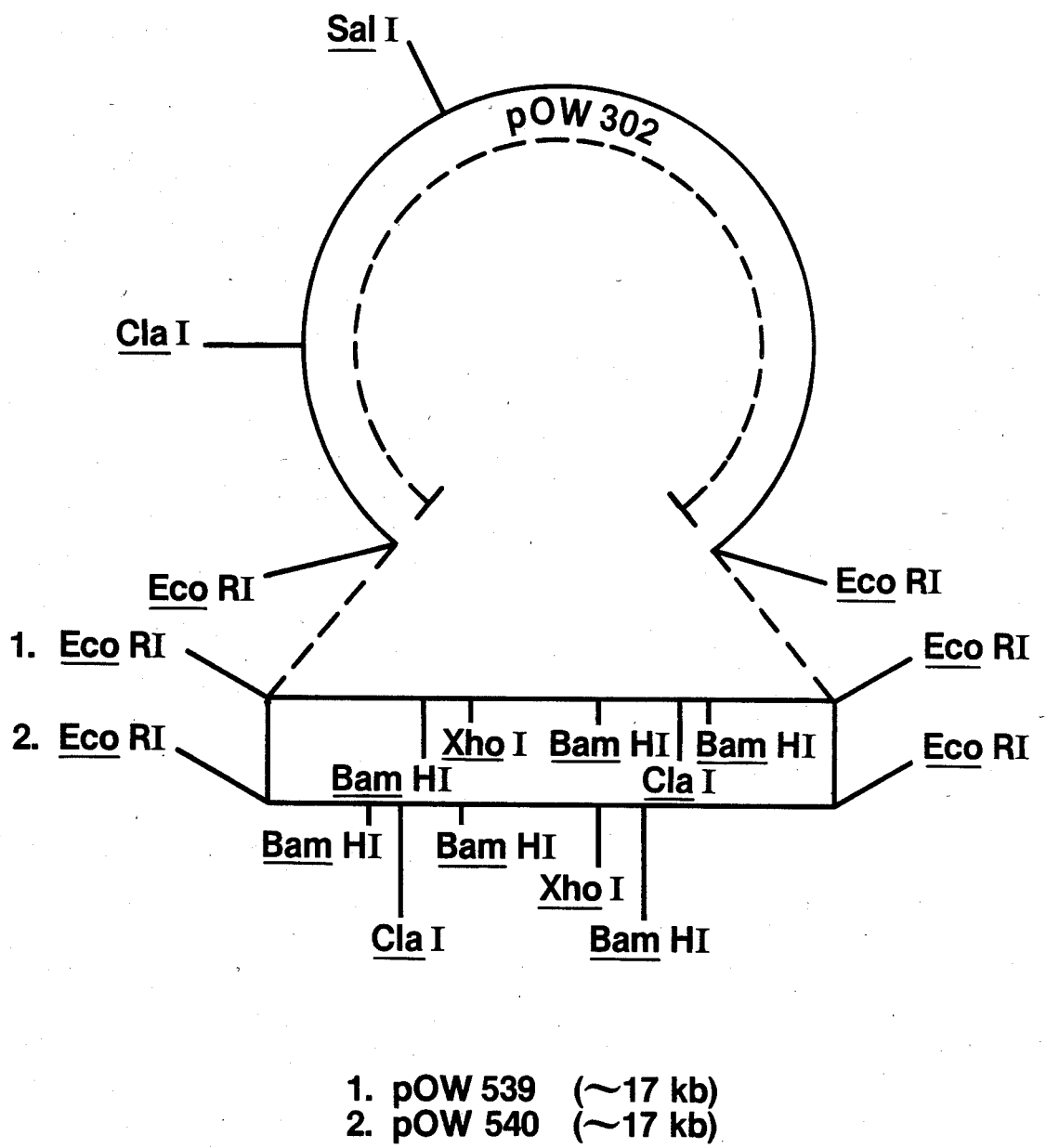

Plasmids pOW539 and pOW540 were constructed for illustrating expression in Streptomyces, under the control of a homologous Bacillus promoter and naturally occurring Bacillus ribosome binding site, of a fused gene product. Accordingly, the aforedescribed ~0.48 kb EcoRI-BamHI fragment of plasmid pMS480 was ligated to the ~9.9 kb EcoRI-BamHI fragment of plasmid pMC1403 resulting in plasmid pOW301. The latter plasmid was BamHI digested, treated with the Klenow fragment of DNA polymerase I and then ligated to produce plasmid pOW302. Plasmid pOW302 is functional in *E. coli* and comprises a portion of the lacZ gene in translational reading phase with the veg promoter, naturally occurring ribosome binding site, and a portion of a gene encoding an homologous *Bacillus subtilis* polypeptide. Plasmid pOW302 was then EcoRI digested and ligated to similarly digested plasmid pBS1. The resulting constructions, designated herein as plasmids pOW539 and pOW540, express a fused gene product conferring β-galactosidase activity in Streptomyces and therefore are useful for exemplifying the present invention. The β-galactosidase activity can be used as a selectable marker making the vectors generally useful for molecular cloning. A restriction site map of each of plasmids pOW539 and pOW540 is presented in FIG. 3 of the accompanying drawings.

The present method is particularly versatile and can be applied to the production in Streptomyces of any polypeptide which can be encoded by a gene in a recombinant DNA cloning vector. A preferred recombinant DNA cloning vector is the plasmid although bacteriophage and other vectors can also be used and are apparent to those skilled in the art. In addition to the illustrative pre-proinsulin and lacZ genes, other genes that can be used include genes that are naturally occurring, genes that are non-naturally occurring and genes that are in part naturally occurring and in part synthetic or non-naturally occurring. More particularly, the genes can code for human proinsulin, human insulin A-chain, human insulin B-chain, non-human insulin, human growth hormone, non-human growth hormone, bovine growth hormone, porcine growth hormone, human interferon, non-human interferon, viral antigen, urokinase, any peptide hormone, any enzyme or virtually any other polypeptide with research or commercial value.

The present method for expressing a functional polypeptide in Streptomyces is not limited to a single species or strain of Streptomyces. To the contrary, the present invention is broadly applicable and can be applied to host cells of many Streptomyces taxa, particularly the restrictionless strains thereof. Restrictionless strains are readily selected and isolated from Streptomyces taxa by conventional procedures well known in the art (Lomovskaya et al., 1980, Microbiological Reviews 44:206). Host cells of restrictionless strains lack restriction enzymes and therefore do not cut or degrade DNA upon transformation. For purposes of the present application, host cells containing restriction enzymes that do not cut any of the restriction sites of the vectors that are useful for illustrating the present invention are also considered restrictionless.

Preferred host cells of restrictionless strains of Streptomyces taxa that produce aminoglycoside antibiotics and in which the present method can be applied and is especially useful, include restrictionless cells of, for example, *S. kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. tenebrarius* (tobramycin, apramycin), *S. lavendulae* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins),

*S. hofuensis* (seldomycin complex), and *S. canus* (ribosyl paromamine).

Preferred host cells of restrictionless strains of Streptomyces taxa that produce macrolide antibiotics and in which the present method can be applied and is especially useful, include restrictionless cells of, for example: *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetylleukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of Streptomyces taxa that produce β-lactam antibiotics and in which the present method can be applied and is especially useful, include restrictionless cells of, for example: *S. lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus,* and *S. sioyaensis* (MM 4550 and MM 13902).

Preferred host cells of restrictionless strains of Streptomyces taxa that produce polyether antibiotics and in which the present method can be applied and is especially useful, include restrictionless cells of, for example: *S. albus* (A204, A28695A and B, salinomycin), *S. hygroscopicus* (A218, emericid, DE3936), A120A, A286-95A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa that produce glycopeptide antibiotics and in which the present method can be applied and is especially useful, include restrictionless cells of, for example: *S. orientalis* and *S. haranomachiensis* (vancomycin); *S. candidus* (A-35512, avoparcin), and *S. eburosporeus* (LL-AM 374).

Preferred host cells of other Streptomyces restrictionless strains in which the present method can be applied and is epecially useful, include restrictionless cells of, for example: *S. coelicolor, S. granuloruber, S. roseosporus, S. lividans, S. espinosus* and *S. azureus.*

While all the embodiments of the present invention are useful, some of the expression vectors and transformants are preferred for applying the present invention. Accordingly, preferred vectors are plasmids pOW527, pOW528, pOW529, pOW530, pOW539 and pOW540 and preferred transformants are *Streptomyces ambofaciens*/pOW527, *S. ambofaciens*/pOW528, *S. ambofaciens*/pOW529, *S. ambofaciens*/pOW530, *S. ambofaciens*/pOW539 and *S. ambofaciens*/pOW540. Of this preferred group, plasmids pOW529 and pOW539 and transformants *S. ambofaciens*/pOW529 and *S. ambofaciens*/pOW539 are most preferred.

The method for expressing functional polypeptides of the present invention has broad utility and helps fill the need for expression vehicles for use in Streptomyces. Thus, the present method allows for the genetic expression in Streptomyces of products now bioproduced in *E. coli* or Bacillus. This is especially advantageous because large scale fermentation of Streptomyces is better known and understood than is fermentation of either *E. coli* or Bacillus. In fact, commercial fermentation of *E. coli* is still highly experimental and fraught with difficulty. The present invention circumvents this problem by providing the alternative of producing compounds now biosynthesized in *E. coli* such as, for example, human insulin, human proinsulin, glucagon, interferon, human growth hormone, bovine growth hormone and the like, in Streptomyces. This can be done because the vectors useful in the present method are highly versatile and can accommodate DNA sequences which encode the aforementioned products. The present method thus allows for flexibility in the choice of hosts and provides a means for using Streptomyces in the bioproduction of polypeptides and other gene products. This was not possible prior to the present invention. Therefore, the use of homologous Bacillus promoters and Bacillus naturally occurring or modified ribosome binding site-containing DNA sequences for the genetic expression of functional polypeptides in Streptomyces allows for the full exploitation of recombinant DNA technology in that industrially important class of microorganisms.

*Streptomyces granuloruber* No. A39912.13/pEL103, *Bacillus subtilis*/MI112/pHI-16, *E. coli* K12 JA221/pMS480, *E. coli* K12 BE904/pMC1403 and *E. coli* K12 JA221/pOW601, as respective sources of plasmids pEL103, pHI-16, pMS480, pMC1403 and pOW601, and *Streptomyces ambofaciens* can be cultured in a number of ways using any of several different media. Carbohydrate sources which are preferred in a culture medium include, for example, molasses, glucose, dextrin, and glycerol, and nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

*Streptomyces granuloruber* No. A39912.13/pEL103 is grown under aerobic culture conditions over a relatively wide pH range of about 5 to 9 at temperatures ranging from about 15° to 40° C. For production of plasmid pEL103 in the greatest quantity, however, it is desirable to start with a culture medium at a pH of about 7.2 and maintain a culture temperature of about 30° C. Culturing *Streptomyces granuloruber* No. A39912.13/pEL103, under the aforementioned conditions, results in a reservoir of cells from which plasmid pEL103 is isolated conveniently by techniques well known in the art.

*Bacillus subtilis* MI112/pHI-16 is grown under aerobic culture conditions over a relatively wide pH range of about 5 to 8.5 at temperatures ranging from about 25° to 45° C. For production of plasmid pHI-16 in the greatest quantity, however, it is desirable to start with a culture medium at a pH of about 7 and maintain a culture temperature of about 37° C. Culturing *Bacillus subtilis* MI112/pHI-16, under the aforementioned conditions, results in a reservoir of cells from which plasmid pHI-16 is isolated conveniently by techniques well known in the art.

*E. coli* K12 JA221/pMS480, *E. coli* K12 BE904/pMC1403 and *E. coli* K12 JA221/pOW601 are each grown under aerobic culture conditions over a relatively wide pH range of about 6.5 to 8 at temperatures ranging from about 25° to 40° C. For production of plasmids pMS480, pMC1403 and pOW601 in the greatest quantity, however, it is desirable to start with a culture medium at a pH of about 7.2 and maintain a culture temperature of about 37° C. Culturing the *E. coli* cells, under the aforementioned conditions, results in a reservoir of cells from which the plasmids are respectively isolated by techniques well known in the art.

The following examples further illustrate and detail the invention disclosed herein. Both an explanation of and the actual procedures for constructing the invention are described where appropriate.

EXAMPLE 1

Construction of Plasmid pOW10

A. Construction of the ~0.38 kb EcoRI-SfaNI Fragment of Plasmid pMS480

1. Isolation of Plasmid pMS480

The bacterium *E. coli* K12 JA221/pMS480 (NRRL B-15258) was cultured in TY broth (1% tryptone, 0.5% yeast extract, 0.5% sodium chloride, pH 7) with 100 μg./ml. of antibiotic ampicillin according to conventional microbiological procedures. After 18 hours incubation, about 0.5 ml. of the culture was transferred to a 1.5 ml. Eppendorf tube and centrifuged for about 15 seconds. Unless otherwise indicated, all the manipulations were done at ambient temperature. The resultant supernatant was carefully removed with a fine-tip aspirator and the cell pellet was suspended in about 100 μl. of freshly prepared lysozyme solution which contained 2 mg./ml. lysozyme, 50 mM glucose, 10 mM EDTA (ethylene diaminetetracetate) and 25 mM Tris-HCl (pH 8). After incubation at 0° C. for 30 minutes, about 200 μl. of alkaline SDS (sodium dodecyl sulfate) solution (0.2N NaOH, 1% SDS) were added and then the tube was gently vortexed and maintained at 0° C. for 5 minutes. Next, about 150 μl. of 3M sodium acetate (prepared by dissolving 3 moles of sodium acetate in a minimum of water, adjusting the pH to 4.8 with glacial acetic acid and then adjusting the volume to 1 l.) were added a DNA clot formed after the contents of the tube were mixed gently for a few seconds by inversion.

The tube was maintained at 0° C. for 60 minutes and then centrifuged for 5 minutes to yield an almost clear supernatant. About 0.4 ml. of the supernatant was transferred to a second centrifuge tube to which 1 ml. of cold ethanol was added. After the tube was held at −20° C. for 30 minutes, the resultant precipitate was collected by centrifugation (2 minutes) and the supernatant was removed by aspiration. The thus collected pellet was dissolved in 200 μl. of 0.1M sodium acetate/0.05M Tris-HCl (pH 8) and was reprecipitated by the addition of 2 volumes of cold ethanol. After 10 minutes at −20° C., the precipitate was collected by centrifugation and constituted the desired plasmid pMS480 DNA.

2. EcoRI-SfaNI Digestion of Plasmid pMS480

About 5 μl. (5 μg.) of plasmid pMS480 (isolated in Example A-1) in TE buffer (10 mM Tris-HCl, pH 8., 1 mM EDTA), 5 μl. DTT (100 mM Dithiothreitol), 5 μl. (1000 μg./ml.) BSA (bovine serum albumin), 25 μl. water, 5 μl. (5 New England Biolab units) EcoRI restriction enzyme* and 5 μl. 10× reaction mix** were incubated at 37° C. for about 1 hour. The reaction was terminated by incubation at 65° C. for 10 minutes. Next, the reaction mixture was cooled on ice and then about 1.1 μl. of 5M NaCl, 4 μl. water and 5 μl. (5 New England Bio lab units) SfaNI restriction enzyme were added followed by a second incubation at 37° C. for 1 hour. The reaction was terminated by incubation at 65° C. for 10 minutes and then the reaction mixture was cooled on ice, extracted with each of phenol and chloroform:isoamyl alcohol (24:1) and then ethanol precipitated. The desired ~0.38 kb EcoRI-SfaNI restriction fragments were conventionally separated and isolated by agarose gel electrophoresis (Maniatis et al., 1982, Molecular Cloning, Cold Spring Harbor Laboratory, Cold Spring Harbor, N.Y.). The desired ~0.38 kb fragments were dissolved in about 30 μl. of water.

*Restriction and other enzymes can be obtained from the following sources:
New England Bio Labs., Inc.
32 Tozer Road
Beverly, Mass. 01915
Boehringer-Mannheim Biochemicals
7941 Castleway Drive
Indianapolis, Ind. 46250
**Reaction mix (10×) for EcoRI restriction enzyme was prepared with the following composition:
500 mM NaCl
1000 mM Tris-HCl, pH7.2
50 mM MgCl₂

B. Construction of the ~4 kb EcoRI-NcoI Fragment of Plasmid pOW601

1. Isolation of Plasmid pOW601

Plasmid pOW601 is isolated from *E. coli* K12 JA221/pOW601 (NRRL B-15259). The strain was cultured and the plasmid was isolated in substantial accordance with the teaching of Example 1A-1.

2. EcoRI-NcoI Digestion of Plasmid pOW601

The desired digestion is carried out in substantial accordance with the teaching of Example 1A-2 except that plasmid pOWA601, rather than plasmid pMS480, was used.

C. Construction of the DNA Fragment

wherein R is G, R$^1$ is C, and R$^2$ is G.

The desired construction involves the synthesis and 5' phosphorylation of oligonucleotides T$_1$ and T$_2$ shown below.

| T$_1$ | 5' | AGTGAGGTGGATGC | 3' |
| T$_2$ | 5' | CATGGCATCCACCT | 3' |

Oligonucleotides T$_1$ and T$_2$ were used to construct the desired DNA fragment having an NcoI sticky terminus. The oligonucleotide synthesis was conventionally done by the modified phosphotriester method using fully protected deoxyribonucleotide building blocks.

Figure 4:
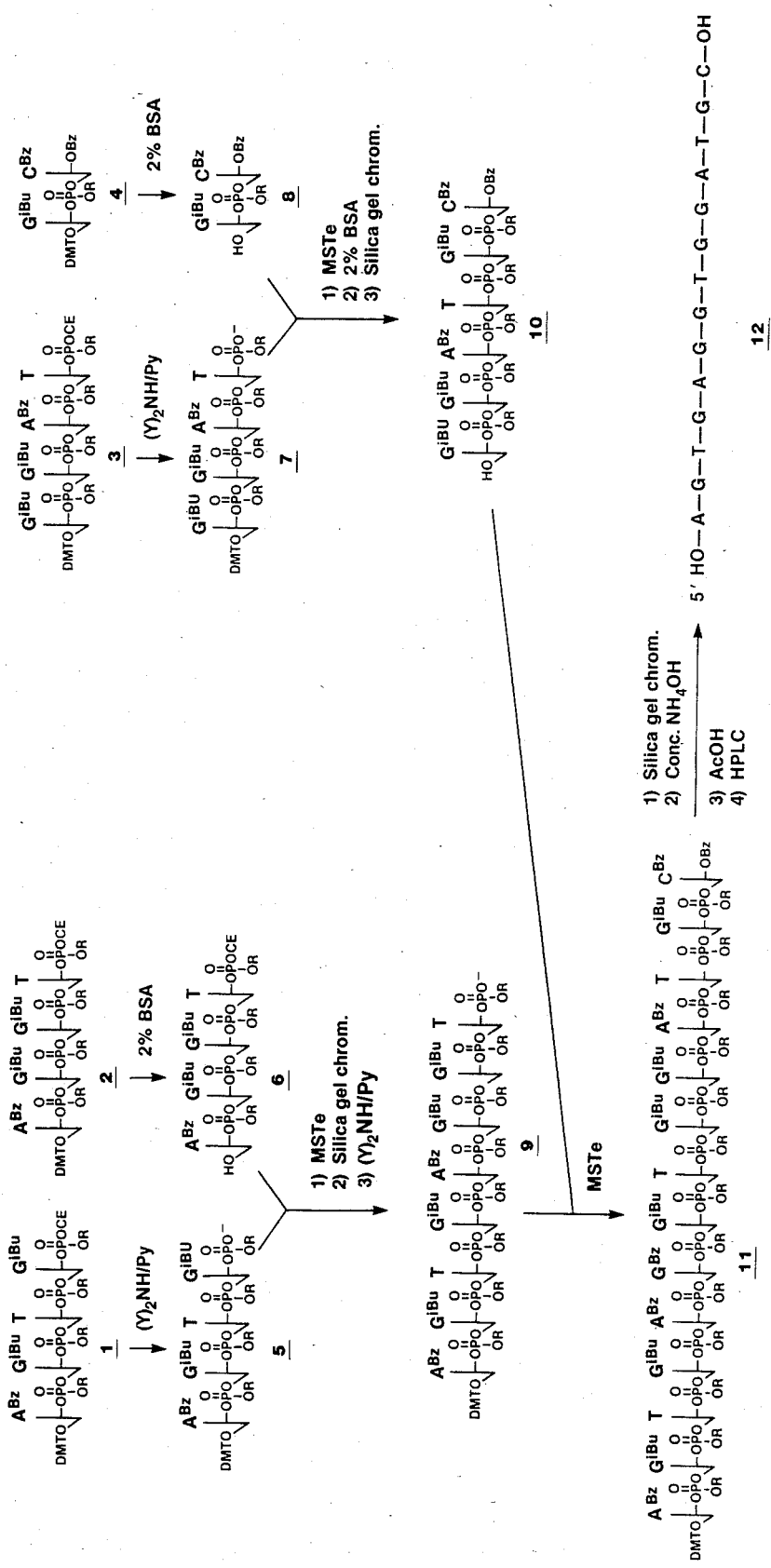

The above synthesis is typified by the following procedure for fragment T$_1$ as summarized in FIG. 4 of the accompanying drawings. Various nucleotide fragments that are used in the synthesis of T$_1$ are numerically designated in the figure. The abbreviations employed are as follows: MSTe, mesitylenesulfonyltetrazole; BSA, benzene sulfonic acid; TLC, thin layer chromatography; HPLC, high performance liquid chromatography; DMT, 4,4'-dimethoxytrityl; CE, 2-cyanoethyl; R, p-chlorophenyl; Bz, benzoyl; (Y)$_2$NH, diisopropylamine; iBu, isobutyryl; Py, pyridine; AcOH, acetic acid.

The fully protected deoxyribotetranucleotides 2 (312 mg., 0.15 mmol) and deoxyribodinucleotides 4 (50 mg., 0.017 mmol) are deblocked at the 5' hydroxyls by treatment with 2% BSA in 7:3 (v/v) chloroform/methanol (2 and 1 ml., respectively) for 10 minutes at 0° C. Reactions are stopped by addition of saturated aqueous ammonium bicarbonate (2 ml.), extracted with chloroform (25 ml), and washed with water (2×, 10 ml.). The organic layers are dried (magnesium sulfate), concentrated to small volumes (about 5 ml.), and precipitated by addition of petroleum ether (35°-60° C. fraction). The colorless precipitates are collected by centrifugation and dried in a dessicator in vacuo to give 6 and 8, respectively, each homogeneous by silica gel tlc (Merck 60 F254, chloroform/methanol, 9:1).

Tetramers 1 and 3 (400 mg., 0.17 mmol; 100 mg., 0.043 mmol) are converted into their phosphodiesters (5 and 6) by treatment with diisopropylamine (1:5, v/v, 2 ml.) for 30 minutes at ambient temperature. The reaction mixture was then precipitated with the addition of anhydrous ether (20 ml.). Reagents are removed by centrifugation and decanting the supernatant. The residues are dried by evaporation with anhydrous pyridine. Dimer 8 (0.04 mmol) and tetramer 7 are combined with MSTe (65 mg., 0.25 mmol) in anhydrous pyridine (1 ml.) and the reaction mixture left at ambient temperature for two hours. TLC analysis shows that 95% of the dimer 8 has been converted into hexamer product (visualized by detection of the DMT group by spraying with 10% aqueous sulfuric acid and heating at 100° C.). The reaction mixture is precipitated by addition of ether and the supernatant is decanted. The hexamer is deblocked at the 5' position with 2% BSA (8 ml.) as described above for dimer 4 and tetramer 2. The product (10) is purified on a silica gel column (Merck 60 H, 3.5×5 cm.) by step gradient elution with chloroform/methanol (98:2 to 95:5, v/v). Fractions containing product 10 are evaporated to dryness.

Similarly, tetramer 5 is coupled to tetramer 6 and the fully protected product directly purified on silica gel. This latter compound is deblocked at the 3' end by diisopropylamine as described above to give fragment 9.

Finally, octamer 9 and hexamer 10 are coupled in anhydrous pyridine (0.5 ml.) with MSTe (100 mg., 0.39 mmol) as the condensing agent. Upon completion (45 minutes, ambient temperature) the mixture is rotary evaporated and the residue chromatographed on silica gel. A portion of compound 11 (20 mg.) in pyridine (0.5 ml.) is completely deblocked by treatment with concentrated ammonium hydroxide (7 ml, 8 hours, 60° C.) and subsequent treatment in 80% acetic acid (15 minutes, ambient temperature). After evaporation of acetic acid, the solid residue is dissolved in distilled water (2 ml.) and extracted with ethyl ether (3×, 2 ml.). The aqueous phase is concentrated to dryness and redissolved in 50% pyridine/water. The product was purified by preparative thin layer chromatography on Polyethyleneimine-Cellulose (PEI/UV$_{254}$) plates (Narang S. A. et al., 1980, Methods in Enzymology 65:610) and then by HPLC on a reverse phase C-18 column (Waters). The sequence of 12 is confirmed by two-dimensional sequence analysis.

Next, oligonucleotide T$_2$ was constructed. This was done in substantial accordance with the above synthesis protocol for oligonucleotide T$_1$.

Ten microgram quantities of the resultant oligonucleotide T$_1$ and T$_2$ are quantitatively phosphorylated with [$\gamma$-$^{32}$P]-ATP (New England Nuclear) in the presence of T$_4$ polynucleotide kinase to give specific activities of approximately 1 Ci/mmol. Radiolabelled fragments are purified by 20% polyacrylamide/7M urea gel electrophoresis and sequences of the eluted fragments are verified by two-dimensional electrophoresis/homochromatography (Jay et al., 1974, Nucleic acids Res. 1:331) of partial snake venom digests. Fragments T$_1$ and T$_2$ are then conventionally annealed to form the desired DNA fragment.

D. Construction of Plasmid pOW10 by ligation of (1) the ~0.38 kb EcoRI-SfaNI Fragment of Plasmid pMS480; (2) the ~4 kb EcoRI-NcoI Fragment of Plasmid pOW601 and (3) the Synthetic DNA Fragment of Example 1C and Construction of E. coli K12 JA221/pOW10.

About 8 μl. (0.01 μg.) of the ~0.38 kb EcoRI-SfaNI fragment of plasmid pMS480, 8 μl. (0.10 μg.) of the ~4 kb EcoRI-NcoI fragment of plasmid pOW601, 10 μl. (0.7 μg.) of the DNA fragment of Example 1C, 10 μl. water, 4 μl. (10 mM)ATP, 2.5 μl. (100 mM) dithiothreitol (DTT), 5 μl. ligation mix** and 2.5 μl. T$_4$ DNA ligase* (~2 New England Bio Lab Units) were incubated at 16° C. for about 16 hours. The reaction was terminated by incubation at 65° C. for 10 minutes and then, after cooling on ice, the resultant ligated mixture was used to transform E. coli K12 JA221 (NRRL B-15211), in substantial accordance with the transformation procedure of Lederberg and Cohen, 1974, J. Bacteriology 119:1072, on TY plate containing 10 μg./ml. of antibiotic tetracycline. The resultant transformants were conventionally cultured and used for subsequent production and isolation of plasmid pOW10 in substantial accordance with the procedure of Example 1A. A restriction site map of plasmid pOW10 is shown in FIG. 1 of the accompanying drawings.

**Ligation mix was prepared with the following composition:
500 mM Tris-HCl, pH 7.6
100 mM MgCl$_2$
*T4 DNA ligase can be obtained from the following source:
New England Bio Labs., Inc.
32 Tozer Rd.
Beverly, Mass. 01915

EXAMPLE 2

Construction of Plasmids pOW527 and pOW528 and *E. coli* K12 JA221/pOW527 and *E. coli* K12 JA221/pOW528

A. Isolation of Plasmid pHI-16

1. Culture of *Bacillus subtilis* MI112/pHI-16

A vegetative culture of *Bacillus subtilis* MI112/pHI-16 (NRRL B-12597) was conventionally prepared by plating on PAB agar (PAB* [Penassay broth] containing agar at 15 g./l. and chloramphenicol at 10 µg./ml.). After the inoculated plate was incubated at 37° C. for about 18 hours, a single colony was selected and used for inoculating 500 ml. of sterilized PAB medium with 10 µg./ml. chloramphenicol. The resultant inoculated broth was incubated at 37° C. for about 18 hours afterwhich the resultant *Bacillus subtilis* MI112/pHI-16 cells were ready for harvest and subsequent isolation of plasmid DNA.
*PAB can be obtained from Difco Laboratories, Detroit Mich.

2. Plasmid Isolation

About 10 g. (wet wgt) of *Bacillus subtilis* MI112/pHI-16 cells were first harvested by centrifugation (10 minutes, 4° C., 10,000 rpm), then washed in about 50 ml. TES (10 mM Tris (pH 8), 10 mM NaCl, 1 mM EDTA) and finally collected again by centrifugation. About 20 ml. TE buffer with 25% sucrose were added to the pellet followed by about 10 mg. of lysozyme in 250 µl. water. The mixture was incubated at 37° C. for about 30 minutes followed by the addition of about 100 units of RNase. The resultant mixture was again incubated at 37° C. for 30 minutes and then, upon being made 1% and 1M with respect to SDS (sodium dodecyl sulfate) and sodium chloride respectively, the mixture was cooled in an ice bath for about 3 hours. After the lysate was centrifuged (30 minutes, 4° C., 19,000 rpm), the supernatent was adjusted to 31.8 ml. with TE and then 28.7 g. of cesium chloride and 0.4 ml. (10 mg./ml.) of ethidium bromide were added. A cesium chloride gradient was established by centrifuging at 49,500 rpm for 16 hours. The plasmid band was collected and centrifuged at 55,000 rpm for 16 hours, then collected again, extracted thrice with equal volumes of isoamyl alcohol, dialyzed against dilute TE, ethanol precipitated, and resuspended in 400 µl. of TE. The resultant plasmid pHI-16 DNA was stored at 4° C. for future use.

The kanamycin resistance gene is contained within the ~0.74 kb HpaII fragment of plasmid pHI-16. Therefore, treatment with HpaII restriction enzyme followed by ligation results in a ~3.9 kb plasmid, designated herein as pHI-18, which lacks the kanamycin resistance gene. A detailed procedure for constructing plasmid pHI-18 is described below.

B. Construction of Plasmid pHI-18

1. Partial HpaII Digestion of Plasmid pHI-16

About 5 µl. (2.5 µg.) of plasmid pHI-16 DNA, 1 µl. (2 mg./ml.) BSA, 37 µl. water, 2 µl. of HpaII (containing 2 New England Bio Labs units) restriction enzyme, and 5 µl. reaction mix* were incubated at 37° C. for 1 hour. After the reaction was terminated by heating at 65° C. for 10 minutes, the DNA was precipitated by adding 2 volumes of 95% ethanol. The resultant DNA precipitate was washed in 70% ethanol, dried in vacuo, suspended in 5 µl. of TE buffer, and stored at 4° C. for future use.
*Reaction mix for HpaII restriction enzyme was prepared with the following composition.
60 mM KCl
100 mM Tris-HCl, pH 7.4
100 mM MgCl$_2$
10 mM Dithiothreitol

2. Ligation of Plasmid pHI-16 HpaII Digest

About 5 µl. of plasmid pHI-16 HpaII digest (prepared in Example 3B-1), 2 µl. T4 DNA ligase, and 43 µl. ligation mix* were incubated at about 16° C. for about 18 hours. The reaction was terminated by the addition of about 5 µl. of 3M sodium acetate and 150 µl. of 95% ethanol. The desired DNA precipitate was washed in 70% ethanol, dried in vacuo, suspended in 10 µl. of TE buffer, and stored at 4° C. for future use.
*Ligation mix was prepared with the following composition:
66 mM Tris-HCl, pH 7.8
10 mM Dithiothreitol
6.6 mM MgCl$_2$
4 mM ATP

C. Construction of *Bacillus subtilis* MI112/pHI-18

*Bacillus subtilis* MI112 can be obtained by conventionally culturing *B. subtilis* MI112/pHI-16 (NRRL B-12597) in the absence of chloramphenicol. The *B. subtilis* MI112/pHI-16 cells spontaneously lose the pHI-16 plasmid under the aforementioned culture conditions thus generating the desired chloramphenicol sensitive *B. subtilis* MI112 strain. Those skilled in the art will recognize and understand that sensitivity to chloramphenicol can be employed for testing and insuring that only *B. subtilis* MI112 cells that lack the plasmid are selected and used in the Bacillus transformation procedures herein disclosed.

About 50 ml. of sterile PAB was inoculated with *Bacillus subtilis* MI112 and incubated at 37° C. until a cell density of $2 \times 10^8$ cells/ml. was reached. The cells were then protoplasted, using sterile technique, by pelleting and then resuspending the cells in about 5 ml. of SMMP (equal volumes of each of 4×PAB and a solution comprising 1.0M sucrose, 0.04M maleic acid, and 0.04M MgCl$_2$, pH adjusted to 6.5 with NaOH). Next, about 250 µl. of lysozyme (20 mg./ml. in SMM [0.5M sucrose, 0.02M maleic acid, and 0.02M MgCl$_2$, pH adjusted to 6.5 with NaOH]) were added using filter sterilization. The cells were incubated with gentle shaking at 37° C. for about 2 hours. The resultant protoplasts were pelleted, washed with 5 ml. SMMP, and then resuspended in 5 ml. SMMP. Following centrifugation (25° C., 12 minutes, 2,600 rpm), about 0.1 ml. of the protoplasts were transformed by adding about 20 µl. of a 1:1 mixture comprising plasmid pHI-18 DNA and 2× SMM. About 1.5 ml. of PEG solution (40 g. PEG 6000 [polyethyleneglycol], 50 ml. 2× SMM, and water to 100 ml.) were then immediately added and, after about 2 minutes, 5 ml. of SMMP were also added. Next, the protoplasts were pelleted, suspended in 1 ml. of SMMP, and incubated at 30° C. with gentle shaking for about 2 hours. Aliquots of the thus prepared suspension were plated on chloramphenicol containing DM3 regeneration medium which per liter had the following composition.

91 g. D-mannitol in 555 ml. deionized water containing 12 g. agar

10% Casamino acids 50 ml.
10% Yeast extract 50 ml.
20% Glucose 25 ml.
5% Dipotassium phosphate 100 ml.
1M MgCl₂ 20 ml.
10% Gelatin
10 mg Chloramphenicol The D-mannitol, casamino acids and yeast extract were autoclaved together. The gelatin was added immediately after autoclaving and the remaining ingredients were added after the mixture had cooled. The medium had a final chloramphenicol concentration of 10 μg./ml.

The resultant chloramphenicol resistant colonies were tested for kanamycin sensitivity. A chloramphenicol resistant and kanamycin sensitive colony was selected as the desired *Bacillus subtilis* MI112/pHI-18 strain. The strain was cultured and the identity further confirmed by conventional restriction enzyme and agarose gel electrophoretic analysis (Maniatis et al., 1982), of the constitutive plasmid.

D. Isolation of Plasmid pEL103

1. Culture of *Streptomyces granuloruber* No. A39912.13/pEL103

A vegetative inoculum of *Streptomyces granuloruber* No. A39912.13/pEL103 (NRRL 12549) was conventionally prepared by growing the strain under submerged aerobic conditions in 50 ml. of sterilized trypticase soy broth* at 35 g./l. in deionized water.

The trypticase soy broth inoculum was incubated for 48 hours at a temperature of 30° C. After incubation, about 10 ml. of the inoculum was transferred to 500 ml. of the sterilized broth and was incubated for about 20 hours at 30° C. The pH was not adjusted. After incubation, the *Streptomyces granuloruber* No. A39912.13/pEL103 cells were ready for harvest and subsequent isolation of plasmid DNA.

*Trypticase soy broth is obtained from BBL Division, Becton-Dickinson & Company, Cockeysville, Md. 21030

2. Plasmid Isolation

About 12 g. (wet wgt) of *Streptomyces granuloruber* No. A39912.13/pEL103 cells were centrifuged (10 minutes, 4° C., 10,000 rpm), washed in 10% glycerol, and then harvested by recentrifugation under the aforementioned conditions. About 50 ml. of TES buffer (0.01M Tris(hydroxymethyl)aminoethane [Tris], 0.001M EDTA, 34% sucrose, pH 8) were added to the cells followed by about 0.25 g. of lysozyme in 10 ml. of 0.25M EDTA. After the mixture was incubated at 37° C. for about 15 minutes, about 0.5 ml. of 10% Triton X-100 in TE buffer (0.01M Tris, 0.001M EDTA, pH 8) was added. The resultant mixture was then incubated at 65° C. for about 15 minutes. After the lysate was centrifuged (45 minutes, 4° C., 18,000 rpm), the supernatant was extracted four times with isoamyl alcohol and once with a chloroformisoamyl alcohol solution (24:1). Next, 0.1 volume of 3M sodium acetate was added to the aqueous phase followed by 3 volumes of cold (−20° C.) 95% ethanol. The ethanol precipitation was rapidly performed in a dry ice-ethanol bath and the DNA precipitate was collected by centrifugation (15 minutes, 4° C., 10,000 rpm). The precipitate was vacuum dried and then resuspended in 1.1 ml. of STE buffer (0.01M Tris, 0.001M EDTA, 0.01M sodium chloride). Centrifugation (40 hours, 15° C., 35,000 rpm) using cesium chloride gradients, with ethidium bromide, was carried out to purify the plasmid DNA. Following centrifugation, the desired plasmid pEL103 DNA band was removed and the ethidium bromide extracted by conventional procedures. After precipitation of the DNA in 3 volumes of ethanol, the thus isolated plasmid pEL103 DNA was dissolved in 1 ml. of 10 fold diluted TE buffer and was then stored at −20° C.

E. Construction of Plasmid pLR2

1. HindIII Digestion of Plasmid pIJ6

About 20 μl. (20 μg.) of plasmid pIJ6 DNA, disclosed in Thompson et al., 1980, Nature 286:525, 5 μl. BSA(-Bovine Serum Albumin, 1 mg./ml.), 19 μl. water, 1 μl. of HindIII (containing 3 New England Bio Labs units) restriction enzyme, and 5 μl. reaction mix* were incubated at 37° C. for 2 hours. The reaction was terminated by the addition of about 50 μl. of 4M ammonium acetate and 200 μl. of 95% ethanol. The resultant DNA precipitate was washed twice in 70% ethanol, dried in vacuo, suspended in 20 μl. of TE buffer, and stored at −20° C.

*Reaction mix for HindIII restriction enzyme was prepared with the following composition.
600 mM NaCl
100 mM Tris-HCl, pH 7.9
70 mM MgCl₂
10 mM Dithiothreitol

2. HindIII Digestion of Plasmid pBR322

About 8 μl. (4 μg.) of plasmid pBR322 DNA*, 5 μl. reaction mix, 5 μl. BSA (1 mg./ml.), 31 μl. water, and 1 μl. of HindIII restriction enzyme were incubated at 37° C. for 2 hours. After the reaction was terminated by incubating at 60° C. for 10 minutes, about 50 μl. of 4M ammonium acetate and 200 μl. of 95% ethanol were added. The resultant DNA precipitate was washed twice in 70% ethanol, dried in vacuo, and suspended in 45 μl. of water.

*Plasmid pBR322 can be obtained from Boehringer-Mannheim Biochemicals the address of which is disclosed in Example 1A-2.

3. Ligation of HindIII Digested Plasmids pIJ6 and pBR322

About 20 μl. of HindIII treated plasmid pIJ6, 20 μl. of HindIII treated plasmid pBR322, 5 μl. BSA (1 mg./ml.), 1 μl. of T4 DNA ligase, and 5 μl. ligation mix* were incubated at 16° C. for 4 hours. The reaction was terminated by the addition of about 50 μl. 4M ammonium acetate and 200 μl. of 95% ethanol. The resultant DNA precipitate was washed twice in 70% ethanol, dried in vacuo, and suspended in TE buffer. The suspended DNA constituted the desired plasmid pLR2.

*Ligation mix was prepared with the following composition.
500 mM Tris-HCl, pH7.8
200 mM Dithiothreitol
100 MgCl₂
10 mM ATP

F. Construction of *E. coli* K12 HB101/pLR2

About 10 ml. of *E. coli* K12 HB101 cells (Bolivar et al., 1977, Gene 2:75-93) were pelleted by centrifugation and then suspended in about 10 ml. of 0.01M sodium chloride. Next, the cells were pelleted again, resuspended in about 10 ml. of 0.03M calcium chloride, incubated on ice for 20 minutes, pelleted a third time, and finally, resuspended in 1.25 ml. of 0.03M calcium chloride. The resultant cell suspension was competent for subsequent transformation.

Plasmid pLR2 in TE buffer was ethanol precipitated, suspended in 150 μl. of 30 mM calcium chloride solution, and gently mixed in a test tube with about 200 μl. of competent *E. coli* K12 HB101 cells. The resultant mixture was incubated on ice for about 45 minutes and then at 42° C. for about 1 minute. Next, about 3 ml. of L-broth (Bertani, 1951, J. Bacteriology 62:293) containing 50 µg./ml. of ampicillin was added. The mixture was incubated with shaking at 37° C. for 1 hour and then plated on L-agar (Miller, 1972, Experiments in Molecular Genetics, Cold Spring Harbor Labs, Cold Spring Harbor, N.Y.) containing ampicillin. Surviving colonies were selected and tested for the expected phenotype (Amp$^R$, Tet$^S$), and constituted the desired *E. coli* K12 HB101/pLR2 transformants.

G. Construction of Plasmids pEL107 and pEL105

1. BamHI Digestion of Plasmid pLR2 and Isolation of the ~1.6 kb Thiostrepton Resistance-Conferring Fragment About 50 µg. of plasmid pLR2 DNA, 10 µl. reaction mix*, 10 µl. BSA (1 mg./ml.), 29 µl. water, and 1 µl. (4 units/µl). of BamHI restriction enzyme were incubated at 37° C. for 2 hours. After adding an equal volume of 4M ammonium acetate and 2.5 volumes of 95% ethanol, the mixture was cooled at −20° C. for about 18 hours to precipitate the DNA. The DNA precipitate was collected by centrifugation and then suspended in about 50 µl. of TE buffer. The desired ~1.6 kb BamHI restriction fragment was isolated conventionally from the DNA suspension by agarose gel electrophoresis (Maniatis et al., 1982). Following isolation, the fragment was resuspended in about 20 µl. of TE buffer for subsequent ligation.

2. Partial BamHI Digestion of Plasmid pEL103

About 20 µg. of plasmid pEL103 DNA, 10 µl. reaction mix, 10 µl. BSA (1 mg./ml.), 39 µl. water, and 1 µl. of BamHI restriction enzyme (prepared by diluting 2 µl. of enzyme in 8 µl. of water) were incubated at ambient temperature for about 15 minutes. After adding an equal volume of 4M ammonium acetate and 2 volumes of 95% ethanol, the mixture was cooled at −20° C. for about 18 hours to precipitate the DNA. The DNA precipitate was collected by centrifugation, rinsed in 70% ethanol, dried in vacuo, and then suspended in about 50 µl. of TE buffer.

3. Ligation

A mixture of about 20 µg. of the partially digest plasmid pEL103 DNA, 10 µg. of the ~1.6 kb BamHI restriction fragment of plasmid pLR2, 5 µl. ligation mix, 5 µl. BSA (1 mg./ml.), 10 µl. water, and 1 µl. T$_4$DNA ligase were incubated at about 16° C. for about 4 hours. After adding 40 µl. of 4M ammonium acetate and 200 µl. of cold ethanol, the mixture was cooled to −20° C. for about 18 hours to precipitate the DNA. The DNA precipitate was collected by centrifugation, washed with 70% ethanol, collected again, and then suspended in 50 µl. of medium P (Hopwood and Wright 1978, Molecular and General Genetics 162:307) for subsequent transformation.

Figure 5:
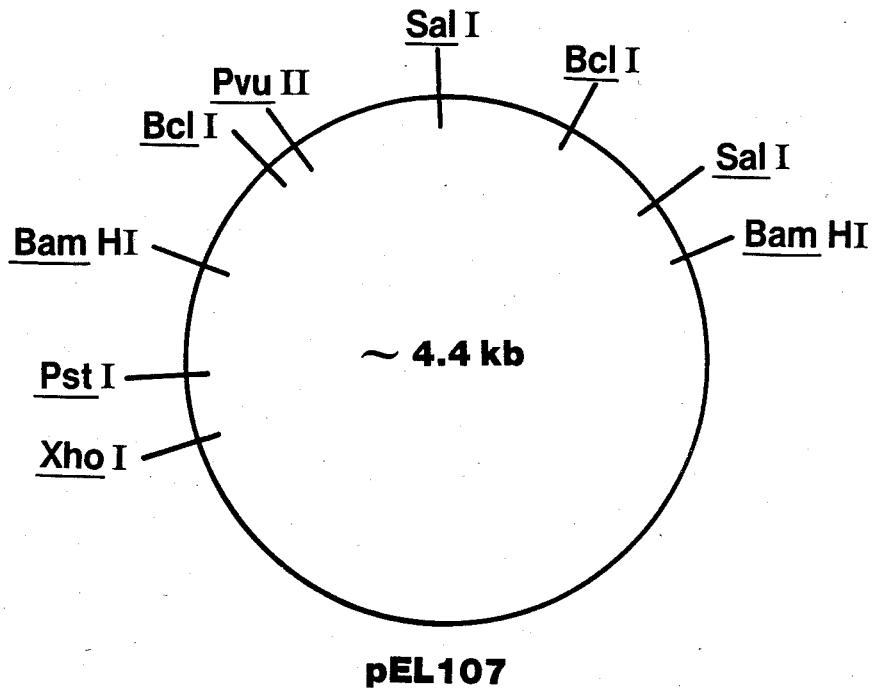
Figure 5:
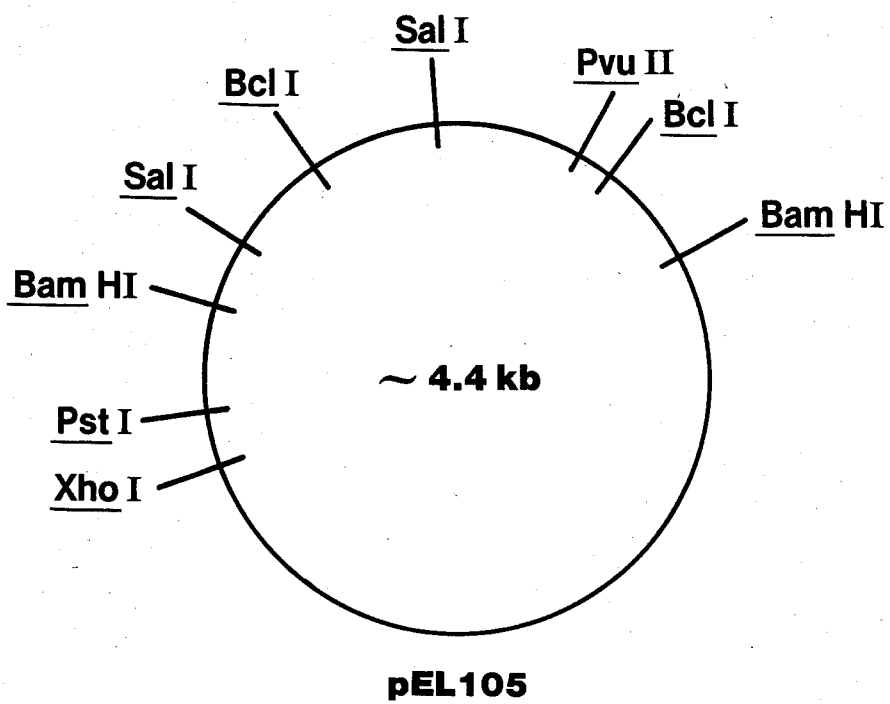

Recombinant plasmids of various types result depending upon which of the possible pEL103 restriction fragments becomes ligated to the ~1.6 kb BamHI thiostrepton resistance conferring fragment. Ligation to the ~2.8 kb BamHI restriction fragment of plasmid pEL103 results in the desired ~4.4 kb plasmids pEL107 and pEL105. Recombinant plasmids of two orientations result because the ~1.6 kb BamHI resistance-conferring fragment can be oriented in either direction. A restriction site and functional map of each of plasmids pEL107 and pEL105 is presented in FIG. 5 of the accompanying drawings.

H. Construction of *Streptomyces ambofaciens*/pEL107 and *S. ambofaciens*/pEL105

Using about 20 µg. of the DNA from Example 2G-3 and 1×10$^8$ protoplasts (prepared according to Baltz, 1978, J. of General Microbiology 107:93) of *Streptomyces ambofaciens*, a strain deposited and made part of the permanent stock culture collection of the Northern Regional Research Laboratory, Peoria, Ill., from which it is available to the public under the accession number NRRL 2420, the desired constructions were made in substantial accordance with the teaching of International Publication (of International Patent Application No. PCT/GB79/00095) No. WO79/01169, Example 2. The desired transformants were selected for thiostrepton resistance by overlaying the regenerating protoplasts with modified R2 medium (Baltz, 1978, J. of General Microbiology 107:93) top agar containing sufficient thiostrepton to bring the final plate concentration to 50 µg./ml. The resultant *Streptomyces ambofaciens*/pEL107 and *S. ambofaciens*/pEL105 thiostrepton resistant colonies were isolated according to known procedures, cultured, and then identified by restriction enzyme and gel electrophoretic analysis (Maniatis et al., 1982), of the constitutive plasmids.

Accordingly, vegetative inocula (10 ml.) of different isolated colonies are conventionally prepared by inoculating trypticase soy broth containing sufficient thiostrepton to bring the final concentration to 50 µg./ml. Several inocula are prepared and the following procedure performed until all the desired transformant types and constitutive plasmids are isolated. Thus, after cells are incubated at 30° C. until fully grown, 6 ml. of the cell-containing broth are centrifuged. The resultant pellet is washed in TE buffer, pelleted again, and then suspended in 400 µl. 50 mM Tris, pH 8.0. Next, about 80 µl. of 0.25M EDTA, 20 µl. RNase, and 100 µl. (10 mg./ml. in TE) lysozyme are added. After the mixture is incubated at 37° C. for about 15 minutes, about 10 µl. of 10% Triton X-100 and 150 µl. 5M NaCl are added followed by a final incubation at 60° C. for 15 minutes. The resultant lysate is centrifuged (15 minutes, 4° C., 15,000 rpm) and then the supernatant is conventionally extracted twice with phenol, once with a chloroform-isoamyl alcohol solution (24:1), and then ethanol precipitated. The identity of the constitutive plasmids and thus the transformants are determined conventionally by restriction enzyme and agarose gel electrophoretic analysis (Maniatis et al., 1982). Plasmid pEL105 was conventionally isolated for subsequent construction of plasmid pBS1.

I. Construction of Plasmids pBS1 and pBS3

1. Partial BamHI Digestion of Plasmid pEL105

About 10 µl. (5 µg.) of plasmid pEL105 (conventionally isolated from *Streptomyces ambofaciens*/pEL105 [prepared in Example 2H] in substantial accordance with the teaching of Example 2A-2), 2 µl. BSA (1 mg./ml.), 29 µl. water, 1 µl. of BamHI (diluted 1:4 with water) restriction enzyme, and 5 µl. reaction mix were incubated at 25° C. for 15 minutes. The reaction was terminated by the addition of about 50 µl. of 4M ammonium acetate and 300 µl. of 95% ethanol. After cooling at −20° C. for about 2 hours, the resultant DNA precipitate was collected by centrifugation, washed twice in 70% ethanol, dried in vacuo, and then suspended in about 10 μl. of TE buffer. Because plasmid pEL105 has two BamHI restriction sites, a mixture of different fragments results.

2. BamHI Digestion of Plasmid pHI-18

About 5 μl. (5 μg.) of plasmid pHI-18, 2 μl. BSA (1 mg./ml.), 9 μl. water, 1 μl. of BamHI (4 units/μl.) restriction enzyme, and 1.5 μl. reaction mix were incubated at 37° C. for about 2 hours. After adding an equal volume of 4M ammonium acetate and 2.5 volumes of 95% ethanol, the mixture was cooled at −20° C. for about 18 hours to precipitate the DNA. The DNA precipitate was collected by centrifugation, washed in 70% ethanol, and then suspended in about 10 μl. of TE buffer.

3. Ligation

About 5 μl. of BamHI-digested plasmid pHI-18, 8 μl. of plasmid pEL105 BamHI partial digest, 27 μl. water, 5 μl. (4 mM) ATP, 5 μl. ligation mix, and 2 μl. T4 DNA ligase were incubated at 16° C. for about 18 hours. The reaction was terminated by the addition of 50 μl. 4M ammonium acetate and 200 μl. of 95% ethanol. After incubation at −20° C. for about 2 hours, the desired plasmid pBS1 and pBS3 DNA precipitate was collected by centrifugation, washed in 70% ethanol, dried in vacuo, suspended in 10 μl. of TE buffer, and stored at 4° C. for future use.

Figure 6:
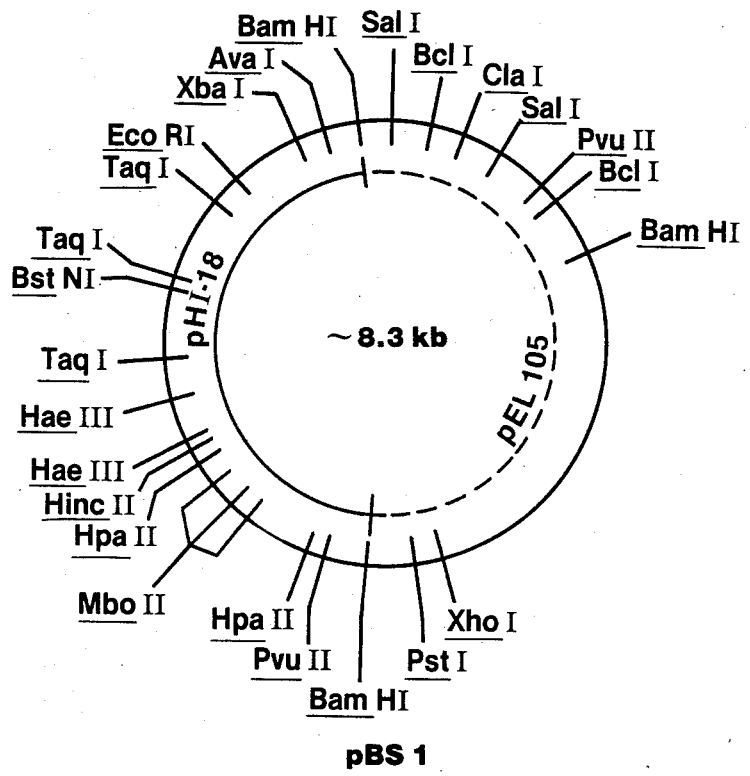
Figure 6:
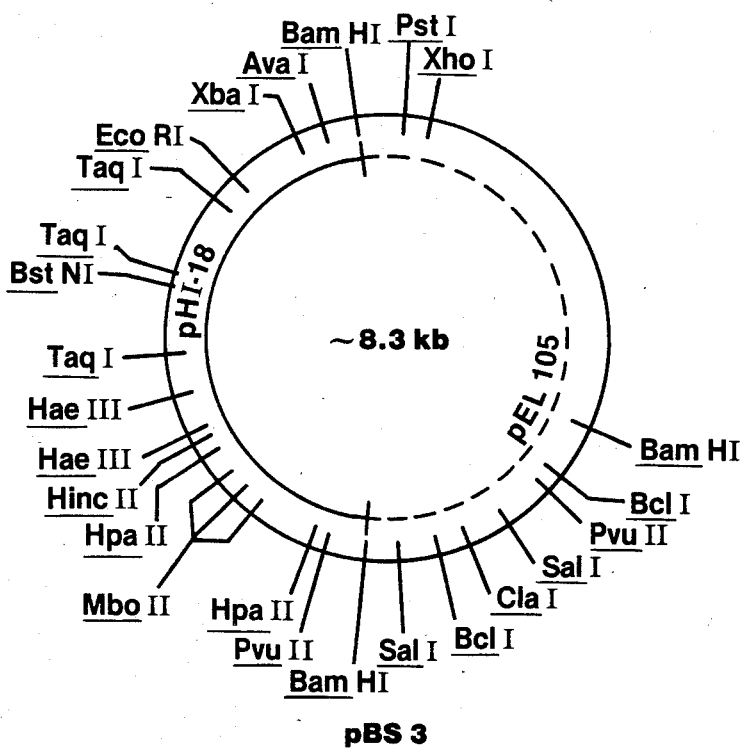

Since plasmid pEL105 has two BamHI restriction sites, a partial BamHI digest results in two ~4.4 kb BamHI fragments. Therefore, the insertional isomers of plasmids pBS1 and pBS3 are also produced by the above procedure. Recombinant plasmids of two orientations result because the BamHI restricted DNA can be ligated in either direction. A restriction site and functional map of each of plasmids pBS1 and pBS3 is presented in FIG. 6 of the accompanying drawings.

J. Construction of *Bacillus subtilis* MI112/pBS1 and *B. subtilis* MI112/pBS3

The desired constructions were made in substantial accordance with the procedure of Example 2C except that plasmids pBS1 and pBS3, rather than plasmid pHI-18, were used. The resultant *Bacillus subtilis* MI112/pBS1 and *B. subtilis* MI112/pBS3 chloramphenicol resistant and kanamycin sensitive transformant colonies were isolated according to known procedures, cultured and then conventionally identified by restriction enzyme and agarose gel electrophoretic analysis (Maniatis et al., 1982), of the constitutive plasmids. *Bacillus subtilis* MI112/pBS1 was selected and cultured for subsequent isolation of plasmid pBS1.

K. Final Construction of Plasmids pOW527 and pOW528 and *E. coli* K12 JA221/pOW527 and *E. coli* K12 JA221/pOW528

1. EcoRI Digestion of Plasmids pBS1 and pOW10

About 4 μl. (3 μg.) of pBS1, 1 μl. (1 μg.) of pOW10, 5 μl. water, 1 μl. 10× EcoRI buffer and 1.5 μl. (containing 5 New England Bio Lab units) EcoRI restriction enzyme were incubated at 37° C. for 1.5 hours. After the reaction was terminated by incubation at 65° C. for 10 minutes, the EcoRI-digested DNA was cooled on ice, ethanol precipitated and then dissolved in 30 μl. of water.

2. Ligation of the Plasmid pBS1 and pOW10 EcoRI Digests and Construction of *E. coli* K12 JA221/pOW527 and *E. coli* K12 JA221/pOW528

About 30 μl. of the pBS1 and pOW10 EcoRI digests, 4 μl. (100 mM) 10× Dithiothreitol, 4 μl. (10 mM) ATP, 4 μl. 10× ligase buffer and 1 μl. (containing 3 New England Bio Lab units) T4 DNA ligase were incubated at 16° C. for about 4 hours. The reaction was terminated by incubation at 65° C. for 10 minutes and then, after cooling on ice, the resultant ligated DNA was used to transform *E. coli* K12 JA221 (NRRL B-15211), in substantial accordance with the transformation procedure of Lederberg and Cohen (1974), on TY plates containing 10 μg./ml. of tetracycline. The resultant transformants were conventionally cultured and used for subsequent production and isolation of plasmids pOW527 and pOW528 in substantial accordance with the procedure of Example 1A. Plasmids pOW527 and pOW528 can be conventionally identified and distinguished by restriction enzyme and agarose gel electrophoretic analysis (Maniatis et al., 1982). Recombinant plasmids of two orientations result because the EcoRI-restricted DNA can be ligated in either direction. A restriction site map of each of plasmids pOW527 and pOW528 is presented in FIG. 1 of the accompanying drawings.

EXAMPLE 3

Construction of *Streptomyces ambofaciens*/pOW527

The desired construction is made in substantial accordance with the teaching of Example 2H except that plasmid pOW527, (prepared in Example 2K), rather than plasmids pEL105 and pEL107, is used. The resultant *Streptomyces ambofaciens*/pOW527 thiostrepton resistant colonies are isolated and cultured according to known procedures. The thus constructed transformants produce pre-proinsulin intracellularly and therefore exemplify the method of the present invention. This is conventionally determined by in vitro assay of cell lysates.

EXAMPLE 4

Construction of *Streptomyces ambofaciens*/pOW528

The desired construction is made in substantial accordance with the teaching of Example 2H except that plasmid pOW528, (prepared in Example 2K), rather than plasmids pEL105 and pEL107, is used. The resultant *Streptomyces ambofaciens*/pOW528 thiostrepton resistant colonies are isolated and cultured according to known procedures. The thus constructed transformants produce pre-proinsulin intracellularly and therefore exemplify the method of the present invention. This is conventionally determined by in vitro assay of cell lysates.

EXAMPLE 5

Construction of Plasmid pOW303 and *E. coli* K12 BE904/pOW303

A. NcoI Digestion of Plasmid pOW10

About 2 μl. (2 μg.) of plasmid pOW10 (prepared in Example 1D), in TE buffer, 2.5 μl. (100 mM) DTT, 0.5 μl. (1000 μg./ml.) BSA, 17 μl. water, 1 μl. (containing 4 New England Bio Lab Units) NcoI restriction enzyme and 2.5 μl. 10× reaction mix* were incubated at 37° C. for 1.5 1 hours. After the reaction was terminated by incubation at 65° C. for 10 minutes, the digested DNA was ethanol precipitated and then dissolved in 34.5 μl. of water.

*Reaction mix for NcoI restriction enzyme was prepared with the following composition.
1500 mM NaCl
60 mM Tris-HCl, pH 7.
60 mM MgCl₂

B. BamHI Digestion of Plasmid pMC1403

The desired digestion was carried out in substantial accordance with the teaching of Example 5A except that plasmid pMC1403 and BamHI restriction enzyme and reaction mix, rather than plasmid pOW10 and NcoI restriction enzyme and reaction mix, were used. Plasmid pMC1403 was isolated from *E. coli* K12 BE904/pMC1403 (NRRL B-15213) in substantial accordance with the teaching of Example 1A-1. The digested DNA was ethanol precipitated and then dissolved in 34.5 μl. of water.

C. Klenow Fill-in of NcoI-Digested Plasmid pOW10 and BamHI-Digested Plasmid pMC1403

The NcoI and BamHI digests of Examples 5A and 5B were combined (69 μl) and then incubated with 4 μl. each of dATP, dGTP, dCTP and TTP, 5 μl. (containing 10 units of DNA polymerase I large (Klenow) fragment* and 10 μl. of 10×Klenow buffer (0.5M Tris-HCl, pH 7.2, 0.1M MgSO₄, 1 mM DTT) at 16° C. for 30 minutes. After the reaction was terminated by incubation at 65° C. for 10 minutes, the DNA was ethanol precipitated, extracted once with phenol and twice with chloroform:isoamyl alcohol (24:1) and then ethanol precipitated again. The Klenow filled-in DNA was dissolved in 20 μl. of water for subsequent EcoRI digestion.

*The Klenow fragment of DNA polymerase I can be obtained from the following source.
Boehringer-Mannheim Biochemicals
7941 Castleway Drive
Indianapolis, Ind. 46250

D. EcoRI Digestion of the Klenow Filled-In NcoI and BamHI Fragments

About 20 μl. (4 μg.) of the Klenow filled-in DNA, 5 μl. (100 mM) DTT, 5 μl. (1000 μg./ml.) BSA, 2 μl. (containing 10 New England Bio Lab Units) EcoRI restriction enzyme and 5 μl. (10×) reaction mix were incubated at 37° C. for 1 hour and then at 65° C. for 10 minutes. The resultant EcoRI-digested DNA was ethanol precipitated and then dissolved in 30 μl. of water.

E. Ligation of the EcoRI-Digested Klenow Filled-In NcoI and BamHI Fragments and Construction of *E. coli* K12 BE904/pOW303

About 30 μl. of the EcoRI-digested Klenow filled-in fragments, 4 μl. (100 mM) DTT, 4 μl. (100 mM) ATP, 4 μl. 10× ligase buffer and 1 μl. (containing 10 New England Bio Lab Units) T₄ DNA ligase were incubated at 16° C. for about 16 hours and then at 65° C. for 10 minutes. After cooling on ice about 15 μl. of the resultant ligated DNA, designated herein as plasmid pOW303, was used to transform *E. coli* K12 BE904 (NRRL B-15212). This was done in substantial accordance with the procedure of Example 1D except that plasmid pOW303, rather than plasmid pOW10, was used and 80 μg./ml. of ampicillin was used instead of tetracycline. In addition, the TY plates contained 40 μg./ml. of 5-bromo-4-chloro-3-indolyl-β-D-galactoside (x-gal) so that color could be used as a convenient assay of β-galactosidase activity. The resultant blue and ampicillin-resistant transformants constituted the desired *E. coli* K12 BE904/pOW303. The transformants were cultured, using conventional microbiological techniques, and were used for subsequent production and isolation of plasmid pOW303 in substantial accordance with the procedure of Example 1A-1. A restriction site map of plasmid pOW303 is presented in FIG. 2 of the accompanying drawings.

EXAMPLE 6

Construction of Plasmids pOW529 and pOW530 and *E. coli* K12 BE904/pOW529 and *E. coli* K12 BE904/pOW530

The desired constructions are made in substantial accordance with the teaching of Examples 2K-1 and 2K-2 except that plasmid pOW303, rather than plasmid pOW10, is used and 80 μg./ml. of ampicillin is used instead of tetracycline. In addition, the TY plates contain 40 μg./ml. of x-gal so that color can be used as a convenient assay of β-galactosidase activity. Recombinant plasmids of two orientations result because the EcoRI-restricted DNA can be ligated in either direction. Plasmids pOW529 and pOW520 were conventionally isolated, distinguished and identified by restriction enzyme and agarose gel electrophoretic analysis (Maniatis et al., 1982). A restriction site map of each of plasmids pOW529 and pOW530 is presented in FIG. 2 of the accompanying drawings.

EXAMPLE 7

Construction of *Streptomyces ambofaciens*/pOW529 and *Streptomyces ambofaciens*/pOW530

The desired constructions are each made in substantial accordance with the teaching of Example 2H except that plasmids pOW529 and pOW530 and LAC⁻ *Streptomyces ambofaciens*, a strain deposited and made part of the permanent stock culture collection of the Northern Regional Research Laboratory, Peoria, Ill., from which it is available to the public under the accession number 15263, rather than plasmids pEL105 and pEL107, and LAC⁺ *Streptomyces ambofaciens* (NRRL 2420), are respectively used. In addition, the modified R2 plates (Baltz, 1978), contain 40 μg./ml. of x-gal so that color can be used as a convenient assay of β-galactosidase activity. The transformants each produce dark blue colonies indicating that the gene encoding β-galactosidase is expressed in Streptomyces. Therefore the constructions further exemplify the method of the present invention. The β-galactosidase activity is further confirmed conventionally by in vitro assay.

EXAMPLE 8

Construction of Plasmid pOW301 and *E. coli* K12 BE904/pOW301

A. EcoRI-BamHI Digestion of Plasmid pMS480

The desired digestion was carried out in substantial accordance with the teaching of Example 1A-2 except that BamHI restriction enzyme, rather than SfaNI restriction enzyme, was used. The fragments were dissolved in about 10 μl. of water and used without further purification.

B. EcoRI-BamHI Digestion of Plasmid pMC1403

The desired digestion was carried out in substantial accordance with the teaching of Example 1A-2 except that BamHI restriction enyzme and plasmid pMC1403 (isolated in Example 5B), rather than SfaNI restriction enzyme and plasmid pMS480, were used. The fragments were dissolved in about 10 μl. of water and used without further purification.

C. Ligation of the EcoRI-BamHI Digests of Plasmids pMS480 and pMC1403

About 10 μl. of the plasmid pMS480 EcoRI-BamHI digest, 10 μl. of the plasmid pMC1403 EcoRI-BamHI digest, 3 μl. (100 mM) DTT, 10 μl. water, 3 μl. (10 mM) ATP, 3 μl. ligation mix* and 1 μl. T4 DNA ligase (containing ~400 New England Bio Lab Units) were incubated for about 12 hours. The reaction was terminated by incubation at 65° C. for 10 minutes and then, after cooling on ice, the resultant ligated mixture was used to transform *E. coli* BE904 (NRRL B-15212) in substantial accordance with the transformantion procedure of Lederberg and Cohen, 1974, on TY plates containing 80 μg./ml. ampicillin.

Some of the resultant transformants, as conventionally shown by agarose gel electrophoresis and other tests, contained the desired ~10.3 kb plasmid. Such a transformant, designated herein as *E. coli* BE904-/pOW301, was selected, plated on TY agar containing 40 μg./ml. of antibiotic ampicillin and then cultured using conventional microbiological techniques. The resultant cells were used to isolate plasmid pOW301 in substantial accordance with the procedure of Example 1A-1.

*Ligation mix was prepared with the following composition:
500 mM Tris-HCl, pH 7.8
100 mM MgCl2

EXAMPLE 9

The veg promoter and the gene which encodes β-galactosidase activity are not in translational reading phase in plasmid pOW301. Therefore, plasmid pOW301 was modified such that the aforementioned reading phase was corrected. This was done in accordance with the procedure outlined below and resulted in plasmid pOW302.

Construction of Plasmid pOW302

A. BamHI Digestion of Plasmid pOW301

About 10 μl. (10 μg.) of plasmid pOW301 in TE buffer, 1 μl. DTT (100 mM Dithiothreitol), 1 μl. (1000 μg./ml.) BSA, 1 μl. (containing 16 New England Bio Lab units) BamHI restriction enzyme and 1.5 μl. 10× reaction mix* were incubated at 37° C. for about 1½ hours. The reaction was terminated by incubation at 65° C. for 10 minutes and then the reaction mixture was cooled on ice, extracted with each of phenol and chloroform:isoamyl alcohol (24:1), ethanol precipitated and then dissolved in 69 μl. of water.

*Reaction mix for BamHI restriction enzyme was prepared with the following composition.
1.5M NaCl
60 mM Tris-HCl, pH 7.9
60 mM MgCl2

B. Treatment of pOW301 Linear DNA with Klenow Fragment and Final Ligation

About 69 μl. of the pOW301 linear DNA, 10 μl. of 10× buffer (0.5M Tris, pH 7.5, 0.1M MgCl2), 4 μl. each of (200 mM) dCTP, dATP, TTP and dGTP and 5 μl. (containing 10 Boehringer-Mannheim Units) of DNA polymerase I large (Klenow) fragment were incubated at 16° C. for 30 minutes. After heat inactivation at 65° C. for 10 minutes, the DNA was ethanol precipitated, dissolved in 20 μl. of water, and then ligated to produce the desired plasmid pOW302. The ligation was carried out by reacting about 20 μl. of the Klenow-treated DNA, 3 μl. (100 mM) DTT, 3 μl. (10 mM) ATP, 3 μl. ligation buffer and 1 μl. (containing 400 New England Bio Lab units) T4 DNA ligase at 16° C. for 2 hours. About 10 μl. of the ligation mixture was used to transform *E. coli* K12 BE904 in substantial accordance with the teaching of Example 1C. Blue colonies developed which indicated that the veg promoter and the gene which encodes β-galactosidase activity were in translational reading phase. A restriction site map of plasmid pOW302 is presented in FIG. 3 of the accompanying drawings.

EXAMPLE 10

Construction of Plasmids pOW539 and pOW 540 and *E. coli* K12 BE904/pOW539 and *E. coli* K12 BE904/pOW540

The desired constructions were made in substantial accordance with the teaching of Examples 2K-1 and 2K-2 except that plasmid pOW302, rather than plasmid pOW10, was used and 80 μg./ml. of ampicillin was used instead of tetracycline. In addition, the TY plates contained 40 μg./ml. of x-gal so that color could be used as a convenient assay of β-galactosidase activity. Recombinant plasmids of two orientations result because the EcoRI-restricted DNA can be ligated in either direction. The resultant transformants were conventionally isolated, cultured, identified by restriction enzyme and agarose gel electrophoretic analysis of their constitutive plasmids (Maniatis et al., 1982), and used for subsequent production of plasmids pOW539 and pOW540. A restriction site map of each of plasmids pOW539 and pOW540 is presented in FIG. 3 of the accompanying drawings.

EXAMPLE 11

Construction of *Streptomyces ambofaciens*/pOW539 and *Streptomyces ambofaciens*/pOW539

The desired constructions are each individually made in substantial accordance with the teaching of Example 2H except that plasmids pOW539 and pOW540 and LAC− *Streptomyces ambofaciens* (NRRL 15263), rather than plasmids pEL105 and pEL107 and LAC+ *Streptomyces ambofaciens* (NRRL 2420), are repectively used. In addition, the modified R2 plates (Baltz, 1978), contain 40 μg./ml. of x-gal so that color can be used as a convenient assay of β-galactosidase activity. The transformants each produce dark blue colonies indicating tha the gene encoding β-galactosidase activity is expressed in Streptomyces. Therefore the constructions further exemplify the method of the present invention. The β-galactosidase activity is further conventionally confirmed by in vitro assay.

EXAMPLE 12

Construction of the DNA Fragment

wherein R is C, R¹ is G and R² is G.

The desired construction involves the synthesis and 5′ phosphorylation of oligonucleotides T3 and T4 shown below.

| T₃ | 5' | AGTGAGGTGGATCC | 3' |
| T₄ | 5' | CATGGGATCCACCT | 3' |

Oligonucleotides T₃ and T₄ were used to construct the desired DNA fragment having an NcoI sticky terminus adjacent to a BamHI restriction site. The oligonucleotide synthesis was conventionally done by the modified phosphotriester method using fully protected deoxyribonucleotide building blocks. The desired construction was made in substantial accordance with the teaching of Example 1C.

EXAMPLE 13

Construction of Plasmid pOW11 and *E. coli* K12 JA221/pOW11

The desired construction is made in substantial accordance with the teaching of Example 1 except that the BamHI restriction site-containing DNA fragment of Example 12, rather than the DNA fragment of Example 1C, is used. The restriction site map of plasmid pOW11 is the same, except for the aforementioned BamHI site, as that shown for plasmid pOW10 in FIG. 1 of the accompanying drawings.

EXAMPLE 14

Construction of Plasmids pOW533 and pOW534 and *E. coli* K12 JA221/pOW533 and *E. coli* K12 JA221/pOW534

The desired constructions are made in substantial accordance with the teaching of Example 2 except that plasmid pOW11, rather than plasmid pOW10, is used. The restriction site map of each of plasmids pOW533 and pOW534 is respectively the same, except for the aforementioned additional BamHI site from the pOW11 fragment, as that shown for plasmids pOW527 and pOW528 in FIG. 1 of the accompanying drawings.

EXAMPLE 15

Construction of *Streptomyces ambofaciens*/pOW533 and *Streptomyces ambofaciens*/pOW534

The desired constructions are respectively made in substantial accordance with the teachings of Examples 3 and 4 except that plasmids pOW533 and pOW534, rather than plasmids pOW527 and pOW528, are respectively used.

EXAMPLE 16

Construction of Plasmid pOW310 and *E. coli* K12 BE904/pOW310

The desired constructions are made in substantial accordance with the teaching of Example 5 except that plasmid pOW11, rather than plasmid pOW10, is used. The restriction site map of plasmid pOW310 is the same, except for the aforementioned additional BamHI site from the pOW11 fragment, as that shown for plasmid pOW303 in FIG. 2 of the accompanying drawings.

EXAMPLE 17

Construction of Plasmids pOW537 and pOW538 and *E. coli* K12 BE904/pOW537 and *E. coli* K12 BE904/pOW538

The desired constructions are made in substantial accordance with the teaching of Example 6 except that plasmid pOW310, rather than plasmid pOW303, is used. The restriction site map of ech of plasmids pOW537 and pOW538 is respectively the same, except for the aforementioned additional BamHI site from the pOW310 fragment, as that shown for plasmids pOW529 and pOW530 in FIG. 2 of the accompanying drawings.

EXAMPLE 18

Construction of *Streptomyces ambofaciens*/pOW537 and *Streptomyces ambofaciens*/pOW538

The desired constructions are each separately made in substantial accordance with the teaching of Example 7 except that plasmids pOW537 and pOW538 and LAC⁻ *Streptomyces ambofaciens* (NRRL 15263), rather than plasmids pOW529 and pOW530 and LAC⁺ *Streptomyces ambofaciens* NRRL 2420, are used.

We claim:

1. A method for expressing a functional polypeptide in Streptomyces comprising transforming a Streptomyces host cell with a recombinant DNA expression vector, said vector comprising
   (1) a homologous Bacillus promoter,
   (2) Bacillus ribosome binding site-containing DNA sequence, and
   (3) a gene encoding a functional polypeptide and culturing said transformed Streptomyces cell under growing conditions, subject to the limitations that said vector replicates and is selectable in said transformed Streptomyces cell and that said promoter and said DNA sequence direct transcription and expression of said gene in said transformed Streptomyces host cell.

2. A method for expressing a functional polypeptide in Streptomyces comprising transforming a Streptomyces host cell with a recombinant DNA expression vector said vector comprising
   (1) the ribosome binding site-containing DNA sequence

wherein
   A is deoxyadenyl,
   G is deoxyguanyl,
   C is deoxycytosyl,
   T is thymidyl,
   R is G or C,
   R¹ is G or C, and
   R² is G or T, (2) the veg promoter of *Bacillus subtilis*, and
   (3) a gene encoding a functional polypeptide, and culturing said transformed Streptomyces cell under growing conditions, subject to the limitations that said vector replicates and is selectable in said transformed Streptomyces cell and that said promoter and said DNA sequence direct transcription and expression of said gene in said transformed Streptomyces host cell, and subject to the further limitation that (1) R and R¹ are not simultaneously the same deoxyribonucleotide and (2) when R² is T, then R is G and R¹ is C.

3. The method of claim 1 wherein the expression vector is a plasmid.

4. The method of claim 2 wherein the expression vector is a plasmid.

5. The method of claim 3 wherein the gene that encodes a functional polypeptide is selected from the group consisting of genes that encode human preproinsulin, human proinsulin, human insulin A-chain, human insulin B-chain, non-human insulin, human growth hormone non-human growth hormone, bovine growth hormone, porcine growth hormone, human interferon, non-human interferon, viral antigen, urokinse, polypeptide hormone and polypeptide enzyme.

6. The method of claim 5 in which the gene encodes human pre-proinsulin.

7. The method of claim 5 in which the gene encodes human proinsulin.

8. The method of claim 5 in which the gene encodes human insulin A-chain.

9. The method of claim 5 in which the gene encodes human insulin B-chain.

10. The method of claim 5 in which the gene encodes non-human insulin.

11. The method of claim 5 in which the gene encodes human growth hormone.

12. The method of claim 5 in which the gene encodes non-human growth hormone.

13. The method of claim 5 in which the gene encodes bovine growth hormone.

14. The method of claim 5 in which the gene encodes porcine growth hormone.

15. The method of claim 5 in which the gene encodes human interferon.

16. The method of claim 5 in which the gene encodes viral antigen.

17. The method of claim 5 in which the gene encodes a polypeptide hormone.

18. the method of claim 5 in which the gene encodes an enzyme.

19. The method of claim 2 wherein the recombinant DNA expression vector is selected from the group consisting of plasmids pOW527, pOW528, pOW529, pOW530, pOW533, pOW534, pOW537, pOW538, pOW539 and pOW540.

20. The method of claim 19 wherein the plasmid is pOW527.

21. The method of claim 19 wherein the plasmid is pOW528.

22. The method of claim 19 wherein the plasmid is pOW529.

23. The method of claim 19 wherein the plasmid is pOW530.

24. The method of claim 19 wherein the plasmid is pOW533.

25. The method of claim 19 wherein the plasmid is pOW534.

26. The method of claim 19 wherein the plasmid is pOW537.

27. The method of claim 19 wherein the plasmid is pOW538.

28. The method of claim 19 wherein the plasmid is pOW539.

29. The method of claim 19 wherein the plasmid is pOW540.

30. The method of claim 2 wherein the ribosome binding site-containing DNA sequence is

```
5' A G T G A G G T G G A T R  C       3'
   | | | | | | | | | |    |
3'         T C C A C C T A R¹ G G T A C 5'
``` wherein
A is deoxyadenyl,
G is deoxyguanyl,
C is deoxycytosyl,
T is thymidyl,
R is G or C, and
R¹ is G or C
subject to the limitation that R and R¹ are not simultaneously the same deoxyribonucleotide.

31. The method of claim 2 in which the transformed Streptomyces host cell is *Streptomyces ambofaciens.*

32. The method of claim 5 in which the transformed Streptomyces host cell is *Streptomyces ambofaciens.*

33. The method of claim 7 in which the transformed Streptomyces host cell is *Streptomyces ambofaciens.*

34. The method of claim 8 in which the transformed Streptomyces host cell is *Streptomyces ambofaciens.*

35. The method of claim 11 in which the transformed Streptomyces host cell is *Streptomyces ambofaciens.*

36. The method of claim 13 in which the transformed Streptomyces host cell is *Streptomyces ambofaciens.*

37. The method of claim 14 in which the transformed Streptomyces host cell is *Streptomyces ambofaciens.*

38. The method of claim 19 in which the transformed Streptomyces host cell is *Streptomyces ambofaciens.*

39. The method of claim 20 in which the transformed Streptomyces host cell is *Streptomyces ambofaciens.*

40. The method of claim 22 in which the transformed Streptomyces host cell is *Streptomyces ambofaciens.*

41. The method of claim 24 in which the transformed Streptomyces host cell is *Streptomyces ambofaciens.*

42. The method of claim 26 in which the transformed Streptomyces host cell is *Streptomyces ambofaciens.*

43. The method of claim 28 in which the transformed Streptomyces host cell is *Streptomyces ambofaciens.*

44. A transformed Streptomyces host cell of claim 1.

45. A transformed Streptomyces host cell of claim 2.

46. The transformed Streptomyces host cell of claim 45 wherein the gene that encodes a functional polypeptide is selected from the group consisting of genes that encode human pre-proinsulin, human proinsulin, human insulin A-chain, human insulin B-chain, non-human insulin, human growth hormone, non-human growth hormone, bovine growth hormone, procine growth hormone, human interferon, non-human interferon, viral antigen, urokinase, polypeptide hormone and polypeptide enzyme.

47. The transformed Streptomyces host cell of claim 46 in which the gene encodes human proinsulin.

48. The transformed Streptomyces host cell of claim 46 in which the gene encodes human insulin A-chain.

49. The transformed Streptomyces host cell of claim 46 in which the gene encodes human growth hormone.

50. The transformed Streptomyces host cell of claim 46 in which the gene encodes bovine growth hormone.

51. The transformed Streptomyces host cell of claim 46 in which the gene encodes porcine growth hormone.

52. The transformed Streptomyces host cell of claim 44 wherein the recombinant DNA expression vector is selected from the group consisting of plasmids pOW527, pOW528, pOW529, pOW530, pOW533, pOW534, pOW537, pOW538, pOW539 and pOW540.

53. The transformed host cell of claim 52 which is *Streptomyces ambofaciens*/pOW527.

54. The transformed host cell of claim 52 which is *Streptomyces ambofaciens*/pOW529.

55. The transformed host cell of claim 52 which is *Streptomyces ambofaciens*/pOW533.

56. The transformed host cell of claim 52 which is *Streptomyces ambofaciens*/pOW537.

57. The transformed host cell of claim 52 which is *Streptomyces ambofaciens*/pOW539.

58. The transformed host cell of claim 52 which is *Streptomyces ambofaciens*/pOW540.

* * * * *

UNITED STATES PATENT AND TRADEMARK OFFICE
CERTIFICATE OF CORRECTION

PATENT NO. : 4,559,300

DATED : December 17, 1985

INVENTOR(S) : Steven Kovacevic, et al.

It is certified that error appears in the above-identified patent and that said Letters Patent is hereby corrected as shown below:

In Claim 1, Part (2) --a-- should be inserted after (2).

In Claim 2, Part (2) should be inserted on line 51 as a new paragraph.

In Claim 5, line 6, "urokinse" should read --urokinase--.

In Claim 18, "the" should read --The--.

In Claim 46, line 38, "procine" should read --porcine--.

Signed and Sealed this

Eleventh Day of April, 1989

Attest:

DONALD J. QUIGG

Attesting Officer

Commissioner of Patents and Trademarks